(12) United States Patent
Galvin et al.

(10) Patent No.: US 11,398,296 B2
(45) Date of Patent: Jul. 26, 2022

(54) DETECTION USING CONCURRENT MELTING CURVES

(71) Applicant: BIOFIRE DIAGNOSTICS, LLC, Salt Lake City, UT (US)

(72) Inventors: Benjamin William Galvin, Salt Lake City, UT (US); Thomas Charles Robbins, Salt Lake City, UT (US); Charles Benjamin Cox, Sandy, UT (US)

(73) Assignee: BIOFIRE DIAGNOSTICS, LLC, Salt Lake City, UT (US)

( * ) Notice: Subject to any disclaimer, the term of this patent is extended or adjusted under 35 U.S.C. 154(b) by 179 days.

(21) Appl. No.: 16/632,823

(22) PCT Filed: Jun. 21, 2018

(86) PCT No.: PCT/US2018/038692
§ 371 (c)(1),
(2) Date: Jan. 21, 2020

(87) PCT Pub. No.: WO2019/018099
PCT Pub. Date: Jan. 24, 2019

(65) Prior Publication Data
US 2021/0147924 A1    May 20, 2021

Related U.S. Application Data

(60) Provisional application No. 62/535,653, filed on Jul. 21, 2017.

(51) Int. Cl.
| | | |
|---|---|---|
| *C12Q 1/6848* | (2018.01) | |
| *C12Q 1/686* | (2018.01) | |
| *C12Q 1/689* | (2018.01) | |
| *C12Q 1/70* | (2006.01) | |
| *G16B 30/00* | (2019.01) | |
| *G16B 40/10* | (2019.01) | |

(52) U.S. Cl.
CPC ............. *G16B 40/10* (2019.02); *C12Q 1/686* (2013.01); *C12Q 1/689* (2013.01); *C12Q 1/6848* (2013.01); *C12Q 1/70* (2013.01); *G16B 30/00* (2019.02)

(58) Field of Classification Search
CPC ........ G16B 40/10; G16B 30/00; C12Q 1/686; C12Q 1/689; C12Q 1/6848; C12Q 1/70; C12Q 2527/101; C12Q 2527/107; C12Q 2561/113; C12Q 2563/107
See application file for complete search history.

(56) References Cited

U.S. PATENT DOCUMENTS

| | | | |
|---|---|---|---|
| 6,387,621 B1 | 5/2002 | Wittwer | |
| 6,645,758 B1 | 11/2003 | Schnipelsky et al. | |
| 6,730,501 B2 | 5/2004 | Eyre et al. | |
| 6,780,617 B2 | 8/2004 | Chen | |
| 7,373,253 B2 | 5/2008 | Eyre | |
| 8,394,608 B2 | 3/2013 | Ririe et al. | |
| 8,895,295 B2 | 11/2014 | Ririe et al. | |
| 9,273,346 B2 * | 3/2016 | Robbins ............. | G01N 33/6803 |
| 9,586,208 B2 | 3/2017 | Ririe | |
| 9,864,832 B2 * | 1/2018 | Houser ................. | G16B 20/20 |
| 2014/0273181 A1 | 9/2014 | Abbott et al. | |
| 2014/0283945 A1 | 9/2014 | Jones et al. | |
| 2015/0118715 A1 | 4/2015 | Wittwer et al. | |
| 2015/0232916 A1 * | 8/2015 | Rasmussen .......... | C12Q 1/6851 |
| | | | 506/9 |

FOREIGN PATENT DOCUMENTS

| | | |
|---|---|---|
| WO | WO-2010/132813 A2 | 11/2010 |
| WO | WO-2012/162613 A2 | 11/2012 |
| WO | WO-2014/039963 A1 | 3/2014 |
| WO | WO-2017/004390 A1 | 1/2017 |

OTHER PUBLICATIONS

Poritz et al., FilmArray, an automated nested multiplex PCR system for multi-pathogen detection: development and application to respiratory tract infection, PLoS One, 6(10):e26047 (2011).
International Application No. PCT/US2018/038692, International Search Report and Written Opinion, dated Sep. 18, 2018.

* cited by examiner

*Primary Examiner* — David C Thomas
(74) *Attorney, Agent, or Firm* — Marshall, Gerstein & Borun LLP; Randall G. Rueth

(57) ABSTRACT

Methods, sample vessels, and instruments are provided for melting curve analysis. A sample is amplified by thermal cycling the sample well between at least an annealing temperature and a denaturation temperature through n cycles, where each cycle includes an in-cycle denaturation step. Fluorescent data is collected during the in-cycle denaturation step of n cycles where n is at least two. Then a composite melting curve is generated using the fluorescent data collected during the denaturation step of each of the n cycles, and the sample is called using the composite melting curve, where the call is a positive or a negative call.

10 Claims, 21 Drawing Sheets

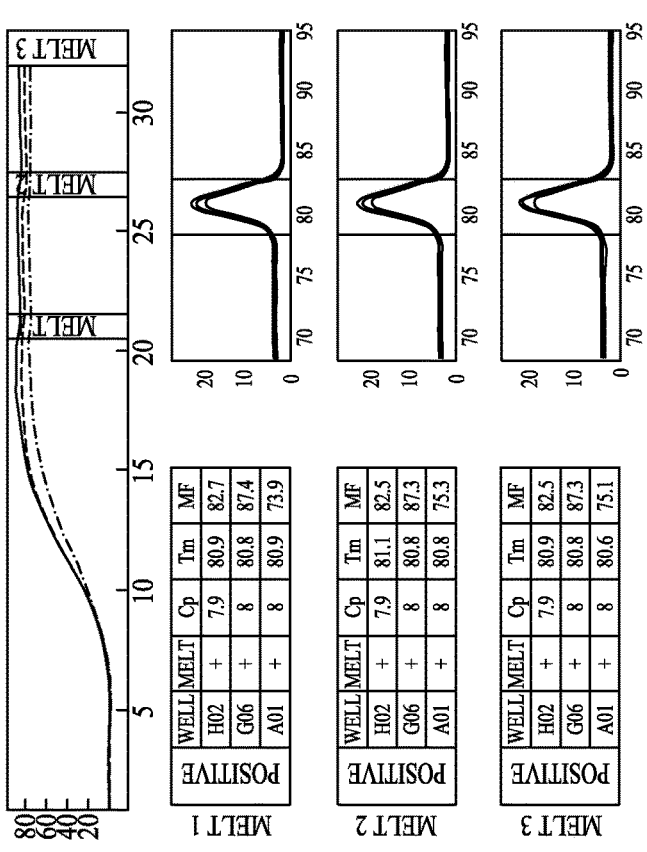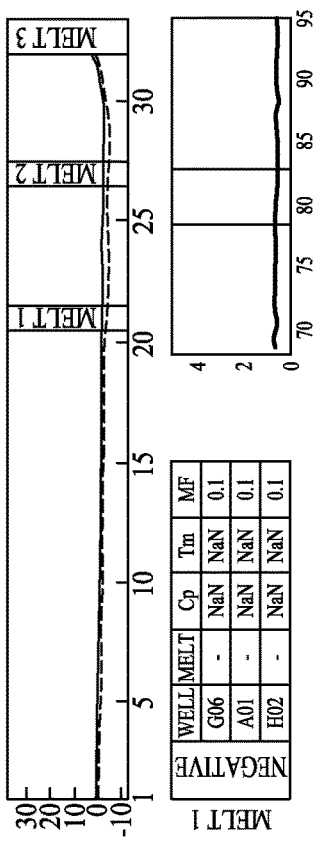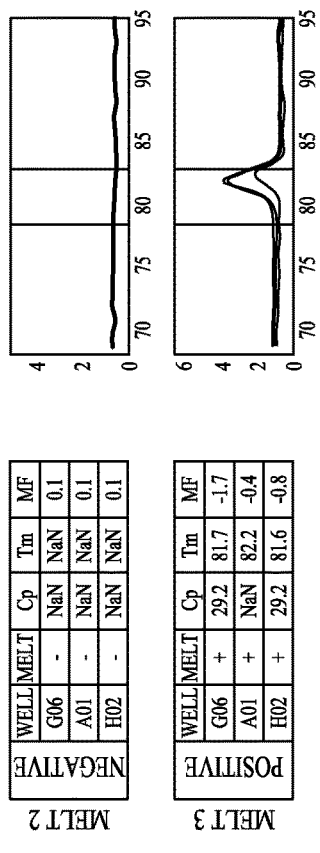
FIG. 5A
FIG. 5B

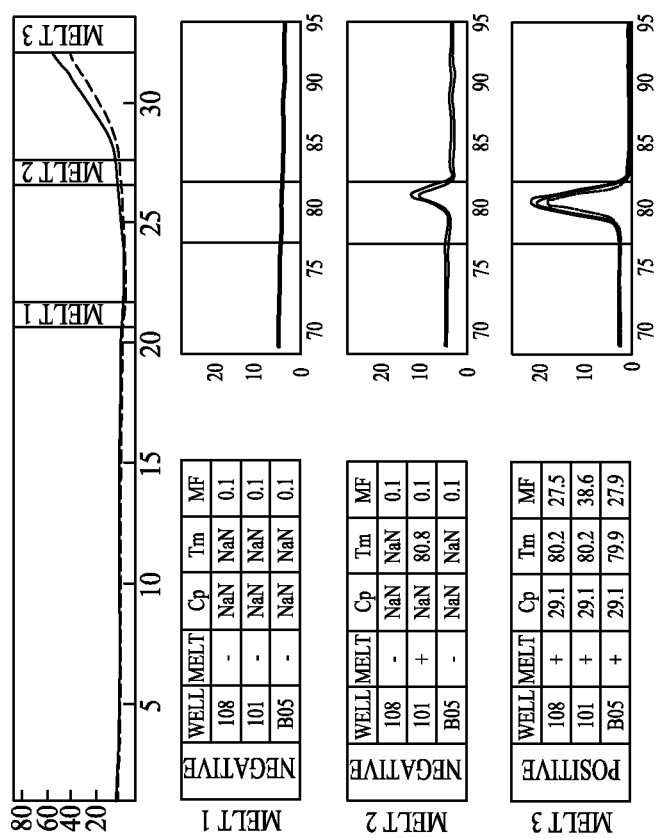
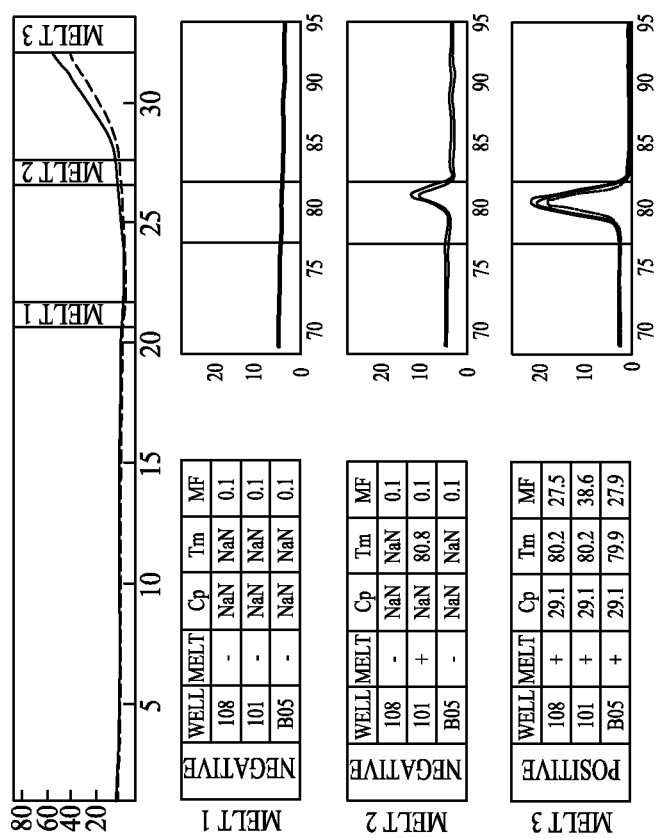
FIG. 6A
FIG. 6B

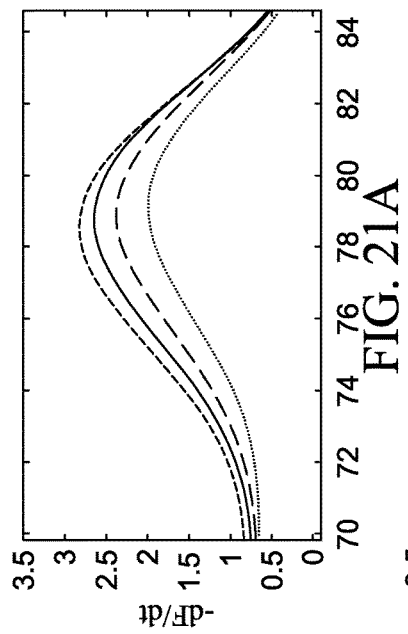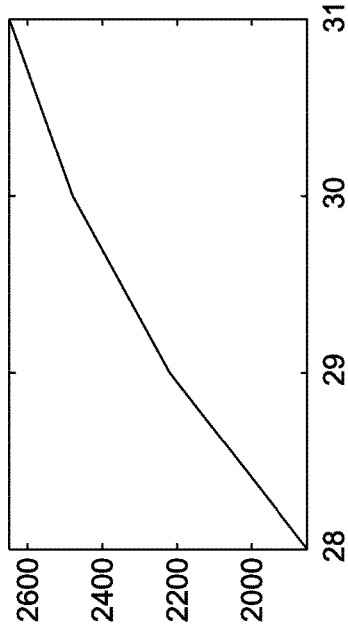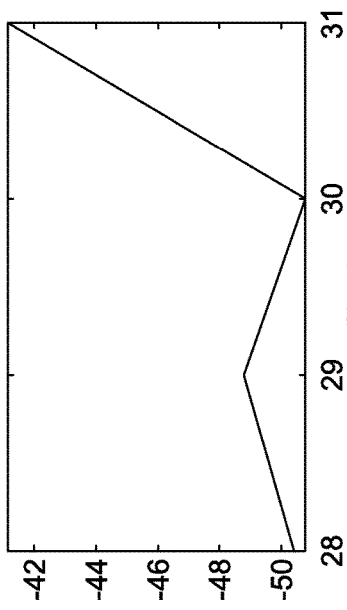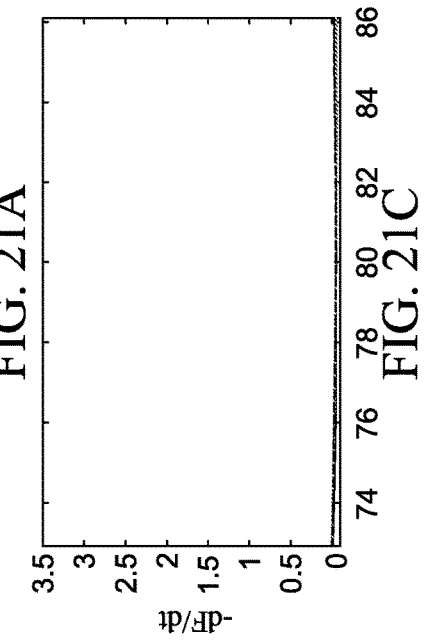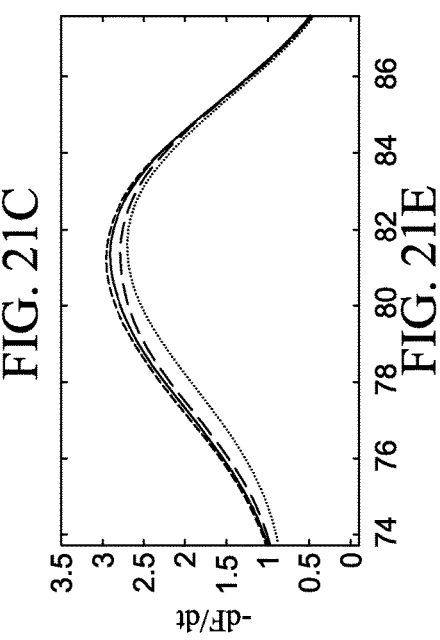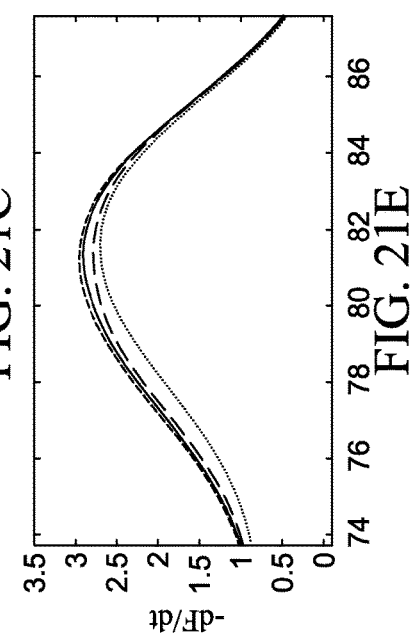
FIG. 21A  FIG. 21B  FIG. 21C  FIG. 21D  FIG. 21E  FIG. 21F

DETECTION USING CONCURRENT MELTING CURVES

CROSS-REFERENCE TO RELATED APPLICATIONS

The present application is a National Stage application of International Application No. PCT/US2018/038692, filed Jun. 21, 2018, which claims priority and the benefit of U.S. Provisional Patent Application No. 62/535,653 entitled "Detection Using Concurrent Melting Curves" and filed on Jul. 21, 2017, the entire disclosures of which are hereby incorporated by reference herein.

BACKGROUND

In the United States, Canada, and Western Europe infectious disease accounts for approximately 7% of human mortality, while in developing regions infectious disease accounts for over 40% of human mortality. Infectious diseases lead to a variety of clinical manifestations. Among common overt manifestations are fever, pneumonia, meningitis, diarrhea, and diarrhea containing blood. While the physical manifestations suggest some pathogens and eliminate others as the etiological agent, a variety of potential causative agents remain, and clear diagnosis often requires a variety of assays to be performed. Traditional microbiology techniques for diagnosing pathogens can take days or weeks, often delaying a proper course of treatment.

In recent years, the polymerase chain reaction (PCR) has become a method of choice for rapid diagnosis of infectious agents. PCR can be a rapid, sensitive, and specific tool to diagnose infectious disease. A challenge to using PCR as a primary means of diagnosis is the variety of possible causative organisms and the low levels of organism present in some pathological specimens. It is often impractical to run large panels of PCR assays, one for each possible causative organism, most of which are expected to be negative. The problem is exacerbated when pathogen nucleic acid is at low concentration and requires a large volume of sample to gather adequate reaction templates. In some cases, there is inadequate sample to assay for all possible etiological agents. A solution is to run "multiplex PCR" wherein the sample is concurrently assayed for multiple targets in a single reaction. While multiplex PCR has proven to be valuable in some systems, shortcomings exist concerning robustness of high level multiplex reactions and difficulties for clear analysis of multiple products. To solve these problems, the assay may be subsequently divided into multiple secondary PCRs. Nesting secondary reactions within the primary product often increases robustness. However, this further handling can be expensive and may lead to contamination or other problems.

Fully integrated multiplex PCR systems integrating sample preparation, amplification, detection, and analysis are user friendly and are particularly well adapted for the diagnostic market and for syndromic approaches. The FilmArray® (BioFire Diagnostics, LLC, Salt Lake City, Utah) is such a system, a user friendly, highly multiplexed PCR system developed for the diagnostic market. The single sample instrument accepts a disposable "pouch" that integrates sample preparation and nested multiplex PCR. Integrated sample preparation provides ease-of-use, while the highly multiplexed PCR provides both the sensitivity of PCR and the ability to test for up to 30 different organisms simultaneously. This system is well suited to pathogen identification where a number of different pathogens all manifest similar clinical symptoms. Current available diagnostic panels include a respiratory panel for upper respiratory infections, a blood culture panel for blood stream infections, a gastrointestinal panel for GI infections, and a meningitis panel for cerebrospinal fluid infections. Other panels are in development.

Positive calls in many PCR systems are made through the use of amplification curves. However, when a dsDNA binding dye is used, it may be difficult to distinguish between amplification of the intended target from non-specific amplification. Moreover, many of the organisms that are targeted in FilmArray panels, as well as in panels for use with other instruments, are commonly present in the environment. While such environmental contamination tends to be present in concentrations that are significantly below that of a clinically relevant sample, it can be difficult to distinguish between environmental contamination and clinical infection. Many of the pathogens targeted by FilmArray panels, as well as other detection systems, are identified by melting curves that are generated during or after amplification. While the Tm of the amplicon can be used to distinguish target amplification from non-specific amplification or to distinguish between alleles or between similar species or strains, the cycle in which the Tm is measured can be used to distinguish between contamination and clinical infection.

In recent years, efforts have been made to increase the speed of PCR, thereby decreasing time to result. As PCR gets faster, the time spent in melting becomes an increasingly larger portion of the run time. However, melting curves generated by faster temperature ramping often result in decreased sensitivity to amplicon differences. It would be desirable to generate melting curves using faster temperature ramping while maintaining sensitivity to amplicon differences.

BRIEF SUMMARY

In one aspect of the present disclosure, methods are provided for calling a sample for a target nucleic acid sequence, the methods comprising providing a sample well with the sample, primers configured for amplifying the target nucleic acid sequence, a fluorescent dye, and components for amplification, amplifying the sample by thermal cycling the sample well between at least an annealing temperature and a denaturation temperature through a plurality of cycles, wherein each cycle includes an in-cycle denaturation step, collecting fluorescent data during the in-cycle denaturation step of n cycles wherein n is at least two, generating a composite melting curve using the fluorescent data collected during the denaturation step of each of the n cycles, and calling the sample using the composite melting curve, wherein the call is selected from at least a positive or a negative call.

In another aspect of the disclosure, systems are provided for calling a sample positive or negative for a target nucleic acid sequence, the illustrative systems comprising a sample well configured to house the sample, the sample well comprising the target nucleic acid and components for amplification; one or more temperature controlling devices configured to amplify the sample by thermal cycling the sample well including heating the sample well to a first temperature and cooling the sample well to a second temperature through a plurality of cycles, wherein each cycle includes an in-cycle temperature adjusting segment, an optical system configured to detect an amount of fluorescence emitted by the sample; a controller configured to receive data indicative of the amount of fluorescence emitted by the sample from an optical system during the in-cycle temperature adjusting segment for two or more of the plurality of cycles, generate a composite melting curve by combining the data from each of the two or more cycles, analyze the composite melting curve to call the sample negative or positive, and display an indication of the negative or positive call for the sample.

In yet another aspect of the disclosure, computing devices are provided for calling a sample positive or negative for a target nucleic acid sequence comprising one or more processors; and a non-transitory computer-readable memory coupled to the one or more processors and storing thereon instructions that, when executed by the one or more processors, cause the computing device to provide control signals to a thermocycling element that include heating the sample to a first temperature and cooling the sample to a second temperature through a plurality of cycles, wherein each cycle includes an in-cycle temperature adjusting segment; receive data indicative of the amount of fluorescence emitted by the sample from an optical system during the in-cycle temperature adjusting segment for two or more of the plurality of cycles; generate a composite melting curve by combining the data from each of the two or more cycles; analyze the composite melting curve to call the sample negative or positive; and display an indication of the call for the sample, wherein the call is selected from at least the positive or negative call.

In still another aspect of the disclosure methods are provided for calling a sample for a target nucleic acid sequence comprising providing a sample well that houses the sample, amplifying the sample by thermal cycling the sample well including heating the sample well to a first temperature and cooling the sample well to a second temperature through a plurality of cycles, wherein each cycle includes an in-cycle temperature adjusting segment, collecting data indicative of the amount of fluorescence emitted by the sample during the in-cycle temperature adjusting segment for two or more of the plurality of cycles, generating, by one or more processors, a composite melting curve by combining the data from each of the two or more cycles, analyzing, by the one or more processors, the composite melting curve to call the sample negative or positive, and displaying, by the one or more processors, an indication of the negative or positive call for the sample.

Additional features and advantages of the embodiments of the invention will be set forth in the description which follows or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 5A-B show amplification and melting curves after three different cycles for A. baumannii. FIG. 5A shows data for a false positive and FIG. 5B shows data for a true positive.

FIGS. 6A-B show amplification and melting curves after three different cycles for C. tropicalis. FIG. 6A shows data for a negative sample and FIG. 6B shows data for a positive sample.

FIG. 7A shows data for a negative sample and FIG. 7B shows data for a positive sample.

FIGS. 20A-C show derivative plots of melting curves for four in-cycle denaturation phases, wherein ( - - - ) is cycle 31, ( . . . ) is cycle 30, ( -. -. -. ) is cycle 29, and (—) is cycle 28, and wherein FIG. 20A is a positive amplification of *Bordetella pertussis* that had not plateaued prior to these cycles, FIG. 20B is a positive amplification of Coronavirus 229E that had reached plateau prior to these cycles, and FIG. 20C is a negative reaction.

FIG. 21A is similar to FIG. 20A, except that the assay is human metapneumovirus. FIG. 21B is a plot of the area under the curve (AUC) for the data of FIG. 21A (solid line), where the dashed line is the average slope. FIGS. 21C-D are similar to FIGS. 21A-B, except for a negative assay for Middle East Respiratory Syndrome Coronavirus. FIGS. 21E-F are similar to FIGS. 21A-B, except for a positive assay for influenza B that plateaued after the first in-cycle denaturation phase.

DETAILED DESCRIPTION

Figure 1:
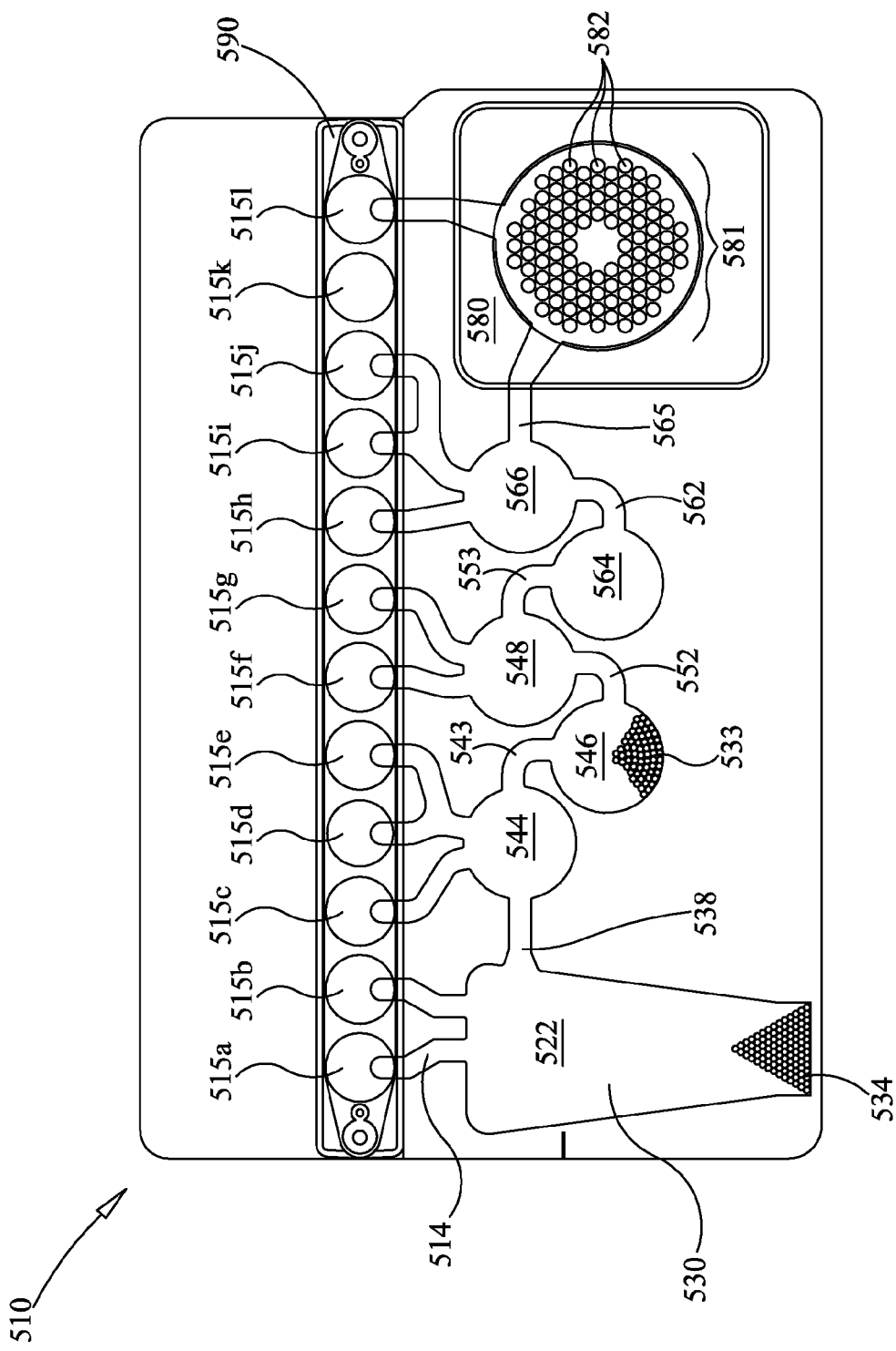
FIG. 1 shows a flexible pouch according to one embodiment of the present invention.

Example embodiments are described below with reference to the accompanying drawings. Many different forms and embodiments are possible without deviating from the spirit and teachings of this disclosure and so the disclosure should not be construed as limited to the example embodiments set forth herein. Rather, these example embodiments are provided so that this disclosure will be thorough and complete, and will convey the scope of the disclosure to those skilled in the art. In the drawings, the sizes and relative sizes of layers and regions may be exaggerated for clarity. Like reference numbers refer to like elements throughout the description.

Unless defined otherwise, all terms (including technical and scientific terms) used herein have the same meaning as commonly understood by one of ordinary skill in the art to which the present disclosure pertains. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. While a number of methods and materials similar or equivalent to those described herein can be used in the practice of the present disclosure, only certain exemplary materials and methods are described herein.

All publications, patent applications, patents or other references mentioned herein are incorporated by reference in their entirety. In case of a conflict in terminology, the present specification is controlling.

Various aspects of the present disclosure, including devices, systems, methods, etc., may be illustrated with reference to one or more exemplary implementations. As used herein, the terms "exemplary" and "illustrative" mean "serving as an example, instance, or illustration," and should not necessarily be construed as preferred or advantageous over other implementations disclosed herein. In addition, reference to an "implementation" or "embodiment" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an," and "the" include plural referents unless the content clearly dictates otherwise. Thus, for example, reference to "a tile" includes one, two, or more tiles. Similarly, reference to a plurality of referents should be interpreted as comprising a single referent and/or a plurality of referents unless the content and/or context clearly dictate otherwise. Thus, reference to "tiles" does not necessarily require a plurality of such tiles. Instead, it will be appreciated that independent of conjugation; one or more tiles are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, directional and/or arbitrary terms, such as "top," "bottom," "left," "right," "up," "down," "upper," "lower," "inner," "outer," "internal," "external," "interior," "exterior," "proximal," "distal," "forward," "reverse," and the like can be used solely to indicate relative directions and/or orientations and may not be otherwise intended to limit the scope of the disclosure, including the specification, invention, and/or claims.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present.

Example embodiments of the present inventive concepts are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments of the present inventive concepts should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of example embodiments.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present embodiments.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g., a polypeptide or nucleic acid); or a solution containing a non-naturally occurring nucleic acid illustratively a cDNA or next-generation sequencing library, which is assayed as described herein. A sample may also be any body fluid or excretion (for example, but not limited to, blood, urine, stool, saliva, tears, bile, or cerebrospinal fluid) that may or may not contain host or pathogen cells, cell components, or nucleic acids.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), modified or treated bases and non-phosphodiester internucleoside linkages (e.g., peptide nucleic acid (PNA) or thiodiester linkages). In particular, nucleic acids can include, without limitation, DNA, cDNA, gDNA, ssDNA, dsDNA, RNA, including all RNA types such as miRNA, mtRNA, rRNA, including coding or non-coding regions, or any combination thereof.

By "probe," "primer," or "oligonucleotide" is meant a single-stranded nucleic acid molecule of defined sequence that can base-pair to a second nucleic acid molecule that contains a complementary sequence (the "target"). The stability of the resulting hybrid depends upon the length, GC content, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes may be used to detect dsDNA. It is understood that a "primer" is specifically configured to be extended by a polymerase, whereas a "probe" or "oligonucleotide" may or may not be so configured. As a probe, the oligonucleotide could be used as part of many fluorescent PCR primer- and probe-based chemistries that are known in the art, including those sharing the use of fluorescence quenching and/or fluorescence resonance energy transfer (FRET) configurations, such as 5'nuclease probes (TaqMan® probes), dual hybridization probes (HybProbes®), or Eclipse® probes or molecular beacons, or Amplifluor® assays, such as Scorpions®, LUX® or QZyme® PCR primers, including those with natural or modified bases.

By "dsDNA binding dyes" is meant dyes that fluoresce differentially when bound to double-stranded DNA than when bound to single-stranded DNA or free in solution, usually by fluorescing more strongly. While reference is made to dsDNA binding dyes, it is understood that any suitable dye may be used herein, with some non-limiting illustrative dyes described in U.S. Pat. No. 7,387,887, herein incorporated by reference. Other signal producing substances may be used for detecting nucleic acid amplification and melting, illustratively enzymes, antibodies, etc., as are known in the art.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant at about melting temperature (Tm) minus 5° C. (i.e., 5° below the Tm of the nucleic acid). Functionally, high stringency conditions are used to identify nucleic acid sequences having at least 80% sequence identity.

While PCR is the amplification method used in the examples herein, it is understood that any amplification method that uses a primer followed by a melting curve may be suitable. Such suitable procedures include polymerase chain reaction (PCR) of any type (single-step, two-steps, or others); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependent amplification (HDA); transcription-mediated amplification (TMA), next generation sequencing techniques, and the like. Therefore, when the term PCR is used, it should be understood to include other alternative amplification methods, including amino acid quantification methods. It is also understood that the methods included herein may be used for other biological and chemical processes that involve thermal cycling followed by melting curve analysis. For amplification methods without discrete cycles, reaction time may be used where measurements are made in cycles or Cp, and additional reaction time may be added where additional PCR cycles are added in the embodiments described herein. It is understood that protocols may need to be adjusted accordingly.

When PCR and other biological and chemical processes that involve thermal cycling are used, it is understood that each cycle includes at least an annealing temperature and a denaturation temperature, wherein the denaturation phase involves heating to the denaturation temperature and the annealing phase involves cooling to the annealing temperature.

While various examples herein reference human targets and human pathogens, these examples are illustrative only. Methods, kits, and devices described herein may be used to detect and sequence a wide variety of nucleic acid sequences from a wide variety of samples, including, human, veterinary, industrial, and environmental.

It is also understood that various implementations described herein can be used in combination with any other implementation described or disclosed, without departing from the scope of the present disclosure. Therefore, products, members, elements, devices, apparatus, systems, methods, processes, compositions, and/or kits according to certain implementations of the present disclosure can include, incorporate, or otherwise comprise properties, features, components, members, elements, steps, and/or the like described in other implementations (including systems, methods, apparatus, and/or the like) disclosed herein without departing from the scope of the present disclosure. Thus, reference to a specific feature in relation to one implementation should not be construed as being limited to applications only within said implementation.

The headings used herein are for organizational purposes only and are not meant to be used to limit the scope of the description or the claims. To facilitate understanding, like reference numerals have been used, where possible, to designate like elements common to the figures. Furthermore, where possible, like numbering of elements have been used in various figures. Furthermore, alternative configurations of a particular element may each include separate letters appended to the element number.

Various embodiments disclosed herein use a self-contained nucleic acid analysis pouch to assay a sample for the presence of various biological substances, illustratively antigens and nucleic acid sequences, illustratively in a single closed system. Such systems, including pouches and instruments for use with the pouches, are disclosed in more detail in U.S. Pat. Nos. 8,394,608; and 8,895,295; and U.S. Patent Application No. 2014-0283945, herein incorporated by reference. However, it is understood that such instruments and pouches are illustrative only, and the nucleic acid preparation and amplification reactions discussed herein may be performed in any of a variety of open or closed system sample vessels as are known in the art, including 96-well plates, plates of other configurations, arrays, carousels, and the like, using a variety of nucleic acid purification and amplification systems, as are known in the art. While the terms "sample well", "amplification well", "amplification container", or the like are used herein, these terms are meant to encompass wells, tubes, and various other reaction containers, as are used in these amplification systems. Such amplification systems may include a single multiplex step in an amplification container and may optionally include a plurality of second-stage individual or lower-order multiplex reactions in a plurality of individual reaction wells. In one embodiment, the pouch is used to assay for multiple pathogens. The pouch may include one or more blisters used as sample wells, illustratively in a closed system. Illustratively, various steps may be performed in the optionally disposable pouch, including nucleic acid preparation, primary large volume multiplex PCR, dilution of primary amplification product, and secondary PCR, culminating with optional real-time detection or post-amplification analysis such as melting-curve analysis. Further, it is understood that while the various steps may be performed in pouches of the present invention, one or more of the steps may be omitted for certain uses, and the pouch configuration may be altered accordingly.

FIG. 1 shows an illustrative pouch 510 that may be used in various embodiments, or may be reconfigured for various embodiments. Pouch 510 is similar to FIG. 15 of U.S. Pat. No. 8,895,295, with like items numbered the same. Fitment 590 is provided with entry channels 515a through 515l, which also serve as reagent reservoirs or waste reservoirs. Illustratively, reagents may be freeze dried in fitment 590 and rehydrated prior to use. Blisters 522, 544, 546, 548, 564, and 566, with their respective channels 514, 538, 543, 552, 553, 562, and 565 are similar to blisters of the same number of FIG. 15 of U.S. Pat. No. 8,895,295. Second-stage reaction zone 580 of FIG. 1 is similar to that of U.S. patent application Ser. No. 8,895,295, but the second-stage wells 582 of high density array 581 are arranged in a somewhat different pattern. The more circular pattern of high density array 581 of FIG. 1 eliminates wells in corners and may result in more uniform filling of second-stage wells 582. As shown, the high density array 581 is provided with 102 second-stage wells 582. Pouch 510 is suitable for use in the FilmArray® instrument (BioFire Diagnostics, LLC, Salt Lake City, Utah). However, it is understood that the pouch embodiment is illustrative only.

While other containers may be used, illustratively, pouch 510 is formed of two layers of a flexible plastic film or other flexible material such as polyester, polyethylene terephthalate (PET), polycarbonate, polypropylene, polymethylmethacrylate, and mixtures thereof that can be made by any process known in the art, including extrusion, plasma deposition, and lamination. Metal foils or plastics with aluminum lamination also may be used. Other barrier materials are known in the art that can be sealed together to form the blisters and channels. If plastic film is used, the layers may be bonded together, illustratively by heat sealing. Illustratively, the material has low nucleic acid binding capacity.

For embodiments employing fluorescent monitoring, plastic films that are adequately low in absorbance and auto-fluorescence at the operative wavelengths are preferred. Such material could be identified by testing different plastics, different plasticizers, and composite ratios, as well as different thicknesses of the film. For plastics with aluminum or other foil lamination, the portion of the pouch that is to be read by a fluorescence detection device can be left without the foil. For example, if fluorescence is monitored in second-stage wells 582 of the second-stage reaction zone 580 of pouch 510, then one or both layers at wells 582 would be left without the foil. In the example of PCR, film laminates composed of polyester (Mylar, DuPont, Wilmington Del.) of about 0.0048 inch (0.1219 mm) thick and polypropylene films of 0.001-0.003 inch (0.025-0.076 mm) thick perform well. Illustratively, pouch 510 is made of a clear material capable of transmitting approximately 80%-90% of incident light.

In the illustrative embodiment, the materials are moved between blisters by the application of pressure, illustratively pneumatic pressure, upon the blisters and channels. Accordingly, in embodiments employing pressure, the pouch material illustratively is flexible enough to allow the pressure to have the desired effect. The term "flexible" is herein used to describe a physical characteristic of the material of pouch. The term "flexible" is herein defined as readily deformable by the levels of pressure used herein without cracking, breaking, crazing, or the like. For example, thin plastic sheets, such as Saran™ wrap and Ziploc® bags, as well as thin metal foil, such as aluminum foil, are flexible. However, only certain regions of the blisters and channels need be flexible, even in embodiments employing pneumatic pressure. Further, only one side of the blisters and channels need to be flexible, as long as the blisters and channels are readily deformable. Other regions of the pouch 510 may be made of a rigid material or may be reinforced with a rigid material.

Illustratively, a plastic film is used for pouch 510. A sheet of metal, illustratively aluminum, or other suitable material, may be milled or otherwise cut, to create a die having a pattern of raised surfaces. When fitted into a pneumatic press (illustratively A-5302-PDS, Janesville Tool Inc., Milton Wis.), illustratively regulated at an operating temperature of 195° C., the pneumatic press works like a printing press, melting the sealing surfaces of plastic film only where the die contacts the film. Various components, such as PCR primers (illustratively spotted onto the film and dried), antigen binding substrates, magnetic beads, and zirconium silicate beads may be sealed inside various blisters as the pouch 510 is formed. Reagents for sample processing can be spotted onto the film prior to sealing, either collectively or separately. In one embodiment, nucleotide tri-phosphates (NTPs) are spotted onto the film separately from polymerase and primers, essentially eliminating activity of the polymerase until the reaction is hydrated by an aqueous sample. If the aqueous sample has been heated prior to hydration, this creates the conditions for a true hot-start PCR and reduces or eliminates the need for expensive chemical hot-start components.

Pouch 510 may be used in a manner similar to that described in U.S. Pat. No. 8,895,295. In one illustrative embodiment, a 300 µl mixture comprising the sample to be tested (100 µl) and lysis buffer (200 µl) is injected into an injection port (not shown) in fitment 590 near entry channel 515a, and the sample mixture is drawn into entry channel 515a. Water is also injected into a second injection port (not shown) of the fitment 590 adjacent entry channel 515l, and is distributed via a channel (not shown) provided in fitment 590, thereby hydrating up to eleven different reagents, each of which were previously provided in dry form at entry channels 515b through 515l. These reagents illustratively may include freeze-dried PCR reagents, DNA extraction reagents, wash solutions, immunoassay reagents, or other chemical entities. Illustratively, the reagents are for nucleic acid extraction, first-stage multiplex PCR, dilution of the multiplex reaction, and preparation of second-stage PCR reagents, as well as control reactions. In the embodiment shown in FIG. 1, all that need be injected is the sample solution in one injection port and water in the other injection port. After injection, the two injection ports may be sealed. For more information on various configurations of pouch 510 and fitment 590, see U.S. Pat. No. 8,895,295, already incorporated by reference.

After injection, the sample is moved from injection channel 515a to lysis blister 522 via channel 514. Lysis blister 522 is provided with beads or particles 534, such as ceramic beads, and is configured for vortexing via impaction using rotating blades or paddles provided within the FilmArray® instrument. Bead-milling, by shaking or vortexing the sample in the presence of lysing particles such as zirconium silicate (ZS) beads 534, is an effective method to form a lysate. It is understood that, as used herein, terms such as "lyse," "lysing," and "lysate" are not limited to rupturing cells, but that such terms include disruption of non-cellular particles, such as viruses.

Figure 2:
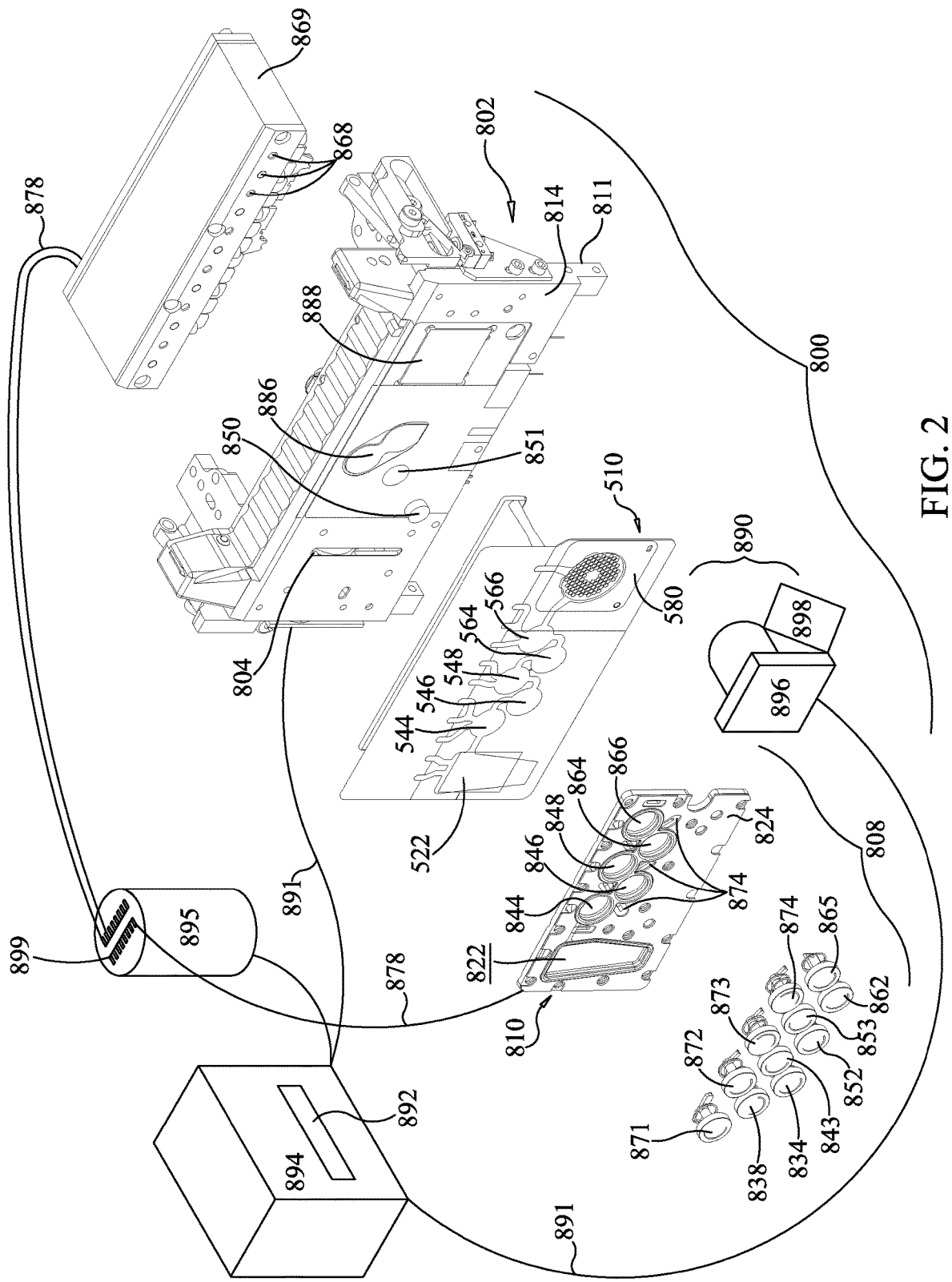
FIG. 2 shows an exploded perspective view of an instrument for use with the pouch of FIG. 1, including the pouch of FIG. 1, according to an example embodiment of the present invention.
Figure 4:
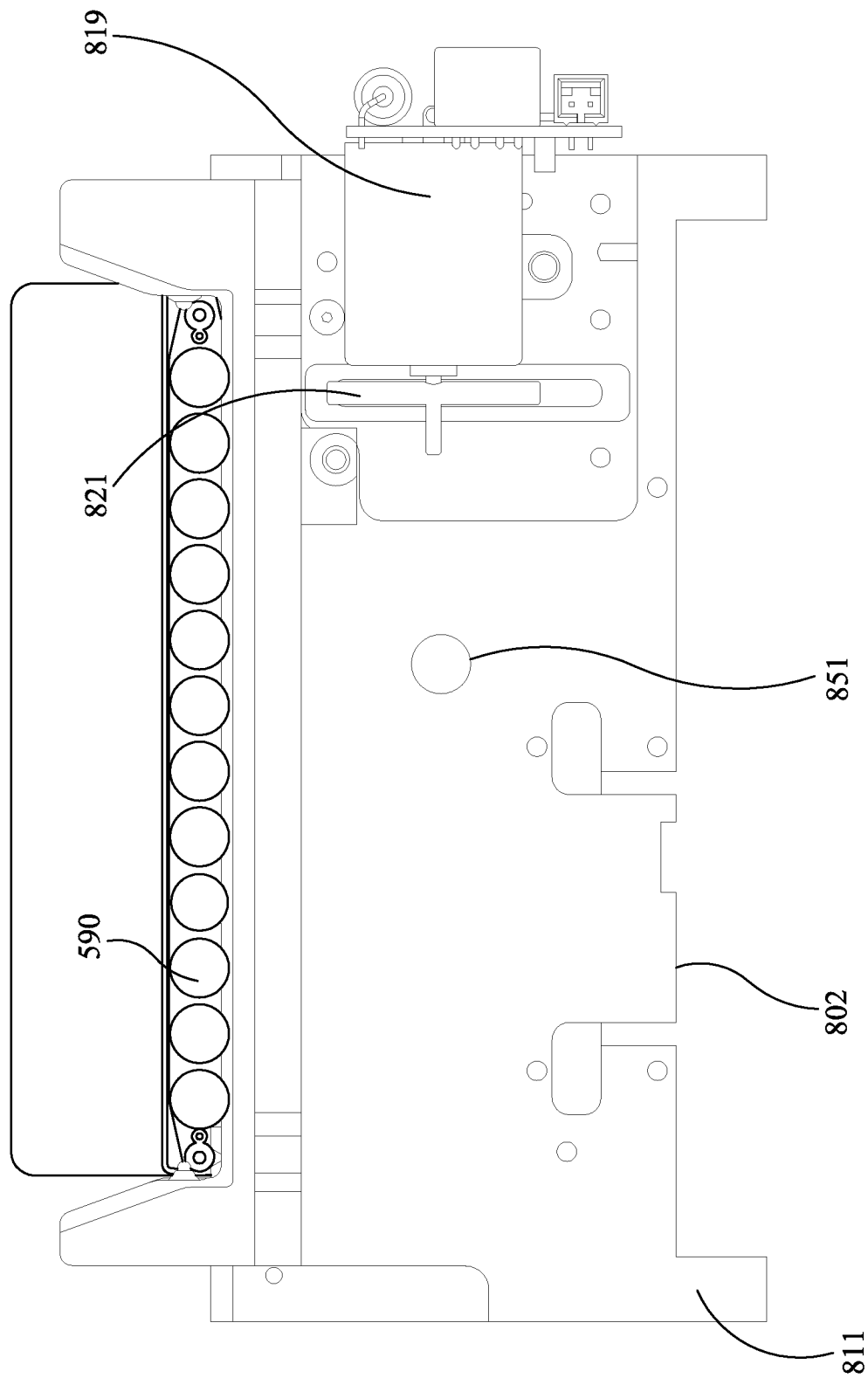
FIG. 4 shows a motor used in one illustrative embodiment of the instrument of FIG. 2.

FIG. 4 shows a bead beating motor 819, comprising blades 821 that may be mounted on a first side 811 of support member 802, of instrument 800 shown in FIG. 2. Blades may extend through slot 804 to contact pouch 510. It is understood, however, that motor 819 may be mounted on other structures of instrument 800. In one illustrative embodiment, motor 819 is a Mabuchi RC-280SA-2865 DC Motor (Chiba, Japan), mounted on support member 802. In one illustrative embodiment, the motor is turned at 5,000 to 25,000 rpm, more illustratively 10,000 to 20,000 rpm, and still more illustratively approximately 15,000 to 18,000 rpm. For the Mabuchi motor, it has been found that 7.2V provides sufficient rpm for lysis. It is understood, however, that the actual speed may be somewhat slower when the blades 821 are impacting pouch 510. Other voltages and speeds may be used for lysis depending on the motor and paddles used. Optionally, controlled small volumes of air may be provided into the bladder 822 adjacent lysis blister 522. It has been found that in some embodiments, partially filling the adjacent bladder with one or more small volumes of air aids in positioning and supporting lysis blister during the lysis process. Alternatively, other structure, illustratively a rigid or compliant gasket or other retaining structure around lysis blister 522, can be used to restrain pouch 510 during lysis. It is also understood that motor 819 is illustrative only, and other devices may be used for milling, shaking, or vortexing the sample.

Once the cells have been adequately lysed, the sample is moved through channel 538, blister 544, and channel 543, to blister 546, where the sample is mixed with a nucleic acid-binding substance, such as silica-coated magnetic beads 533. The mixture is allowed to incubate for an appropriate length of time, illustratively approximately 10 seconds to 10 minutes. A retractable magnet located within the instrument adjacent blister 546 captures the magnetic beads 533 from the solution, forming a pellet against the interior surface of blister 546. The liquid is then moved out of blister 546 and back through blister 544 and into blister 522, which is now used as a waste receptacle. One or more wash buffers from one or more of injection channels 515c to 515e are provided via blister 544 and channel 543 to blister 546. Optionally, the magnet is retracted and the magnetic beads 533 are washed by moving the beads back and forth from blisters 544 and 546 via channel 543. Once the magnetic beads 533 are washed, the magnetic beads 533 are recaptured in blister 546 by activation of the magnet, and the wash solution is then moved to blister 522. This process may be repeated as necessary to wash the lysis buffer and sample debris from the nucleic acid-binding magnetic beads 533.

After washing, elution buffer stored at injection channel 515f is moved to blister 548, and the magnet is retracted. The solution is cycled between blisters 546 and 548 via channel 552, breaking up the pellet of magnetic beads 533 in blister 546 and allowing the captured nucleic acids to dissociate from the beads and come into solution. The magnet is once again activated, capturing the magnetic beads 533 in blister 546, and the eluted nucleic acid solution is moved into blister 548.

First-stage PCR master mix from injection channel 515g is mixed with the nucleic acid sample in blister 548. Optionally, the mixture is mixed by forcing the mixture between 548 and 564 via channel 553. After several cycles of mixing, the solution is contained in blister 564, where a pellet of first-stage PCR primers is provided, at least one set of primers for each target, and first-stage multiplex PCR is performed. If RNA targets are present, a reverse-transcription (RT) step may be performed prior to or simultaneously with the first-stage multiplex PCR. First-stage multiplex PCR temperature cycling in the FilmArray® instrument is illustratively performed for 15-30 cycles, although other levels of amplification may be desirable, depending on the requirements of the specific application. The first-stage PCR master mix may be any of various master mixes, as are known in the art. In one illustrative example, the first-stage PCR master mix may be any of the chemistries disclosed in US2015/0118715, herein incorporated by reference, for use with PCR protocols taking 20 seconds or less per cycle.

After first-stage PCR has proceeded for the desired number of cycles, the sample may be diluted, illustratively by forcing most of the sample back into blister 548, leaving only a small amount in blister 564, and adding second-stage PCR master mix from injection channel 515i. Alternatively, a dilution buffer from 515i may be moved to blister 566 then mixed with the amplified sample in blister 564 by moving the fluids back and forth between blisters 564 and 566. If desired, dilution may be repeated several times, using dilution buffer from injection channels 515j and 515k, or injection channel 515k may be reserved for sequencing or for other post-PCR analysis, and then adding second-stage PCR master mix from injection channel 515h to some or all of the diluted amplified sample. It is understood that the level of dilution may be adjusted by altering the number of dilution steps or by altering the percentage of the sample discarded prior to mixing with the dilution buffer or second-stage PCR master mix comprising components for amplification, illustratively a polymerase, dNTPs, and a suitable buffer, although other components may be suitable, particularly for non-PCR amplification methods. If desired, this mixture of the sample and second-stage PCR master mix may be pre-heated in blister 564 prior to movement to second-stage wells 582 for second-stage amplification. Such preheating may obviate the need for a hot-start component (antibody, chemical, or otherwise) in the second-stage PCR mixture.

The illustrative second-stage PCR master mix is incomplete, lacking primer pairs, and each of the 102 second-stage wells 582 is pre-loaded with a specific PCR primer pair (or sometimes multiple pairs of primers). If desired, second-stage PCR master mix may lack other reaction components, and these components may be pre-loaded in the second-stage wells 582 as well. Each primer pair may be similar to or identical to a first-stage PCR primer pair or may be nested within the first-stage primer pair. Movement of the sample from blister 564 to the second-stage wells 582 completes the PCR reaction mixture. Once high density array 581 is filled, the individual second-stage reactions are sealed in their respective second-stage blisters by any number of means, as is known in the art. Illustrative ways of filling and sealing the high density array 581 without cross-contamination are discussed in U.S. Pat. No. 8,895,295, already incorporated by reference. Illustratively, the various reactions in wells 582 of high density array 581 are simultaneously thermal cycled, illustratively with one or more Peltier devices, although other means for thermal cycling are known in the art.

In certain embodiments, second-stage PCR master mix contains the dsDNA binding dye LCGreen® Plus (BioFire Diagnostics, LLC) to generate a signal indicative of amplification. However, it is understood that this dye is illustrative only, and that other signals may be used, including other dsDNA binding dyes and probes that are labeled fluorescently, radioactively, chemiluminescently, enzymatically, or the like, as are known in the art. Alternatively, wells 582 of array 581 may be provided without a signal, with results reported through subsequent processing.

Figure 3:
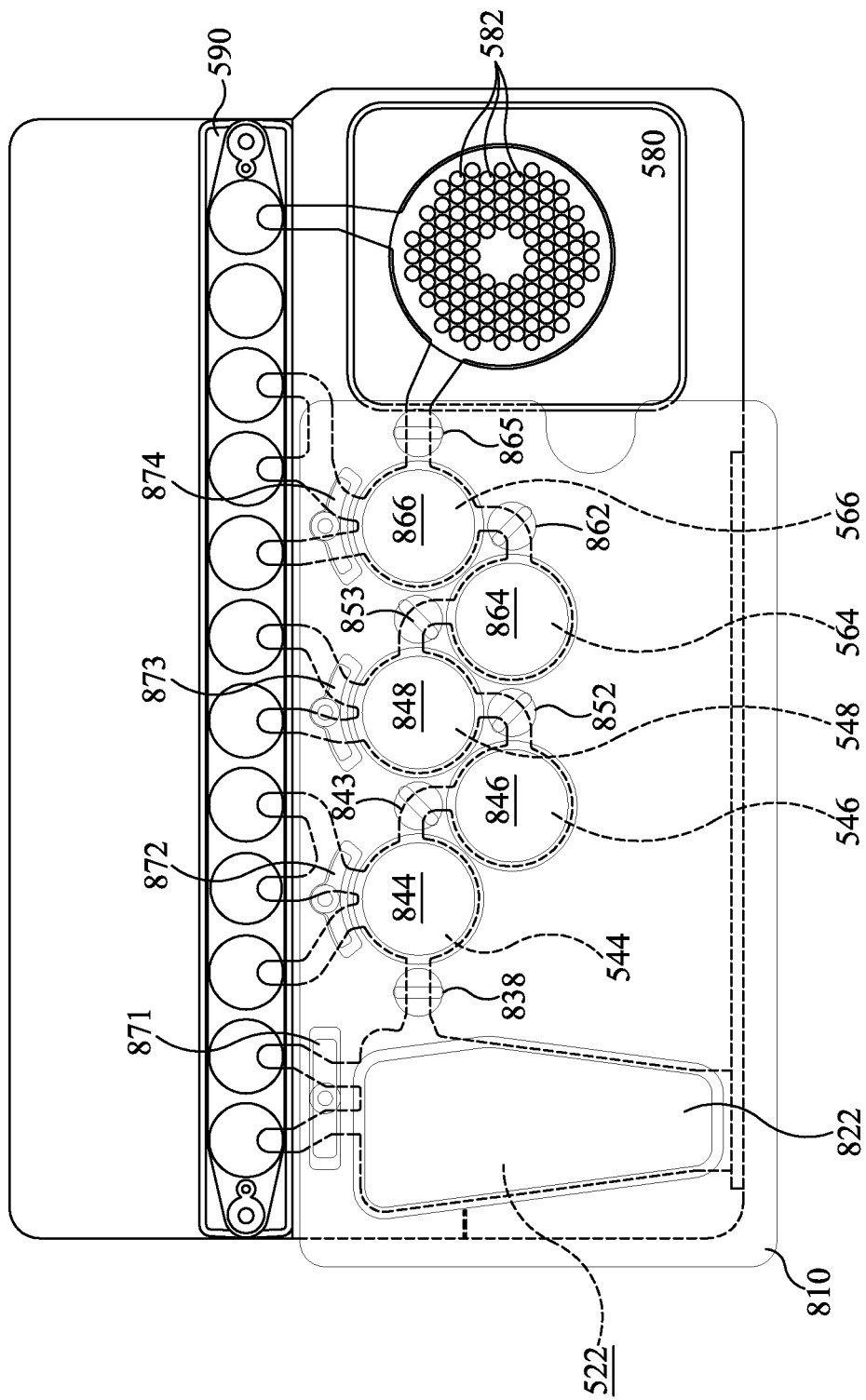
FIG. 3 shows a partial cross-sectional view of the instrument of FIG. 2, including the bladder components of FIG. 2, with the pouch of FIG. 1 shown in dashed lines, according to an example embodiment of the present invention.

When pneumatic pressure is used to move materials within pouch 510, in one embodiment a "bladder" may be employed. The bladder assembly 810, a portion of which is shown in FIGS. 2 and 3, includes a bladder plate 824 housing a plurality of inflatable bladders 822, 844, 846, 848, 864, and 866, each of which may be individually inflatable, illustratively by a compressed gas source. Because the bladder assembly 810 may be subjected to compressed gas and used multiple times, the bladder assembly 810 may be made from tougher or thicker material than the pouch. Alternatively, bladders 822, 844, 846, 848, 864, and 866 may be formed from a series of plates fastened together with gaskets, seals, valves, and pistons. Other arrangements are within the scope of this invention.

Success of the secondary PCR reactions is dependent upon template generated by the multiplex first-stage reaction. Typically, PCR is performed using DNA of high purity. Methods such as phenol extraction or commercial DNA extraction kits provide DNA of high purity. Samples processed through the pouch 510 may require accommodations be made to compensate for a less pure preparation. PCR may be inhibited by components of biological samples, which is a potential obstacle. Illustratively, hot-start PCR, higher concentration of taq polymerase enzyme, adjustments in $MgCl_2$ concentration, adjustments in primer concentration, and addition of adjuvants (such as DMSO, TMSO, or glycerol) optionally may be used to compensate for lower nucleic acid purity. While purity issues are likely to be more of a concern with first-stage amplification and single-stage PCR, it is understood that similar adjustments may be provided in the second-stage amplification as well.

When pouch 510 is placed within the instrument 800, the bladder assembly 810 is pressed against one face of the pouch 510, so that if a particular bladder is inflated, the pressure will force the liquid out of the corresponding blister in the pouch 510. In addition to bladders corresponding to many of the blisters of pouch 510, the bladder assembly 810 may have additional pneumatic actuators, such as bladders or pneumatically-driven pistons, corresponding to various channels of pouch 510. FIGS. 2 and 3 show an illustrative plurality of pistons or hard seals 838, 843, 852, 853, and 865 that correspond to channels 538, 543, 553, and 565 of pouch 510, as well as seals 871, 872, 873, 874 that minimize backflow into fitment 590. When activated, hard seals 838, 843, 852, 853, and 865 form pinch valves to pinch off and close the corresponding channels. To confine liquid within a particular blister of pouch 510, the hard seals are activated over the channels leading to and from the blister, such that the actuators function as pinch valves to pinch the channels shut. Illustratively, to mix two volumes of liquid in different blisters, the pinch valve actuator sealing the connecting channel is activated, and the pneumatic bladders over the blisters are alternately pressurized, forcing the liquid back and forth through the channel connecting the blisters to mix the liquid therein. The pinch valve actuators may be of various shapes and sizes and may be configured to pinch off more than one channel at a time. While pneumatic actuators are discussed herein, it is understood that other ways of providing pressure to the pouch are contemplated, including various electromechanical actuators such as linear stepper motors, motor-driven cams, rigid paddles driven by pneumatic, hydraulic or electromagnetic forces, rollers, rockerarms, and in some cases, cocked springs. In addition, there are a variety of methods of reversibly or irreversibly closing channels in addition to applying pressure normal to the axis of the channel. These include kinking the bag across the channel, heat-sealing, rolling an actuator, and a variety of physical valves sealed into the channel such as butterfly valves and ball valves. Additionally, small Peltier devices or other temperature regulators may be placed adjacent the channels and set at a temperature sufficient to freeze the fluid, effectively forming a seal. Also, while the design of FIG. 1 is adapted for an automated instrument featuring actuator elements positioned over each of the blisters and channels, it is also contemplated that the actuators could remain stationary, and the pouch 510 could be transitioned in one or two dimensions such that a small number of actuators could be used for several of the processing stations including sample disruption, nucleic-acid capture, first and second-stage PCR, and other applications of the pouch 510 such as immuno-assay and immuno-PCR. Rollers acting on channels and blisters could prove particularly useful in a configuration in which the pouch 510 is translated between stations. Thus, while pneumatic actuators are used in the presently disclosed embodiments, when the term "pneumatic actuator" is used herein, it is understood that other actuators and other ways of providing pressure may be used, depending on the configuration of the pouch and the instrument.

Other prior art instruments teach PCR within a sealed flexible container. See, e.g., U.S. Pat. Nos. 6,645,758 and 6,780,617, and 9,586,208, herein incorporated by reference. However, including the cell lysis within the sealed PCR vessel can improve ease of use and safety, particularly if the sample to be tested may contain a biohazard. In the embodiments illustrated herein, the waste from cell lysis, as well as that from all other steps, remains within the sealed pouch. However, it is understood that the pouch contents could be removed for further testing.

FIG. 2 shows an illustrative instrument 800 that could be used with pouch 510. Instrument 800 includes a support member 802 that could form a wall of a casing or be mounted within a casing. Instrument 800 may also include a second support member (not shown) that is optionally movable with respect to support member 802, to allow insertion and withdrawal of pouch 510. Illustratively, a lid may cover pouch 510 once pouch 510 has been inserted into instrument 800. In another embodiment, both support members may be fixed, with pouch 510 held into place by other mechanical means or by pneumatic pressure.

In the illustrative example, heaters 886 and 888 are mounted on support member 802. However, it is understood that this arrangement is illustrative only and that other arrangements are possible. Bladder plate 810, with bladders 822, 844, 846, 848, 864, 866, hard seals 838, 843, 852, 853, seals 871, 872, 873, 874 form bladder assembly 808 may illustratively be mounted on a moveable support structure that may be moved toward pouch 510, such that the pneumatic actuators are placed in contact with pouch 510. When pouch 510 is inserted into instrument 800 and the movable support member is moved toward support member 802, the various blisters of pouch 510 are in a position adjacent to the various bladders of bladder assembly 810 and the various seals of assembly 808, such that activation of the pneumatic actuators may force liquid from one or more of the blisters of pouch 510 or may form pinch valves with one or more channels of pouch 510. The relationship between the blisters and channels of pouch 510 and the bladders and seals of assembly 808 is illustrated in more detail in FIG. 3.

Each pneumatic actuator is connected to compressed air source 895 via valves 899. While only several hoses 878 are shown in FIG. 2, it is understood that each pneumatic fitting is connected via a hose 878 to the compressed gas source 895. Compressed gas source 895 may be a compressor, or, alternatively, compressed gas source 895 may be a compressed gas cylinder, such as a carbon dioxide cylinder. Compressed gas cylinders are particularly useful if portability is desired. Other sources of compressed gas are within the scope of this invention.

Assembly 808 is illustratively mounted on a movable support member, although it is understood that other configurations are possible.

Several other components of instrument 810 are also connected to compressed gas source 895. A magnet 850, which is mounted on a second side 814 of support member 802, is illustratively deployed and retracted using gas from compressed gas source 895 via hose 878, although other methods of moving magnet 850 are known in the art. Magnet 850 sits in recess 851 in support member 802. It is understood that recess 851 can be a passageway through support member 802, so that magnet 850 can contact blister 546 of pouch 510. However, depending on the material of support member 802, it is understood that recess 851 need not extend all the way through support member 802, as long as when magnet 850 is deployed, magnet 850 is close enough to provide a sufficient magnetic field at blister 546, and when magnet 850 is retracted, magnet 850 does not significantly affect any magnetic beads 533 present in blister 546. While reference is made to retracting magnet 850, it is understood that an electromagnet may be used and the electromagnet may be activated and inactivated by controlling flow of electricity through the electromagnet. Thus, while this specification discusses withdrawing or retracting the magnet, it is understood that these terms are broad enough to incorporate other ways of withdrawing the magnetic field. It is understood that the pneumatic connections may be pneumatic hoses or pneumatic air manifolds, thus reducing the number of hoses or valves required.

The various pneumatic pistons 868 of pneumatic piston array 869 are also connected to compressed gas source 895 via hoses 878. While only two hoses 878 are shown connecting pneumatic pistons 868 to compressed gas source 895, it is understood that each of the pneumatic pistons 868 are connected to compressed gas source 895. Twelve pneumatic pistons 868 are shown.

A pair of heating/cooling devices, illustratively Peltier heaters, are mounted on a second side 814 of support 802. First-stage heater 886 is positioned to heat and cool the contents of blister 564 for first-stage PCR. Second-stage heater 888 is positioned to heat and cool the contents of second-stage blisters 582 of pouch 510, for second-stage PCR. It is understood, however, that these heaters could also be used for other heating purposes, and that other heaters may be use, as appropriate for the particular application. Other configurations are possible.

When fluorescent detection is desired, an optical array 890 may be provided. As shown in FIG. 2, optical array 890 includes a light source 898, illustratively a filtered LED light source, filtered white light, or laser illumination, and a camera 896. Camera 896 illustratively has a plurality of photodetectors each corresponding to a second-stage well 582 in pouch 510. Alternatively, camera 896 may take images that contain all of the second-stage wells 582, and the image may be divided into separate fields corresponding to each of the second-stage wells 582. Depending on the configuration, optical array 890 may be stationary, or optical array 890 may be placed on movers attached to one or more motors and moved to obtain signals from each individual second-stage well 582. It is understood that other arrangements are possible.

As shown, a computer 894 controls valves 899 of compressed air source 895, and thus controls all of the pneumatics of instrument 800. Computer 894 also controls heaters 886 and 888, and optical array 890. Each of these components is connected electrically, illustratively via cables 891, although other physical or wireless connections are within the scope of this invention. It is understood that computer 894 may be housed within instrument 800 or may be external to instrument 800. Further, computer 894 may include built-in circuit boards that control some or all of the components, may calculate amplification curves, melting curves, Cps, Cts, standard curves, and other related data, and may also include an external computer, such as a desktop or laptop PC, to receive and display data from the optical array. An interface, illustratively a keyboard interface, may be provided including keys for inputting information and variables such as temperatures, cycle times, etc. Illustratively, a display 892 is also provided. Display 892 may be an LED, LCD, or other such display, for example.

EXAMPLE 1

The FilmArray Blood Culture Identification (BCID) system is designed to provide rapid identification of a broad range of microorganism pathogens directly from blood culture. The illustrative BCID Panel detects the most common bacteria and yeast isolated from positive aerobic blood cultures (PABC), as well as select antibiotic resistance genes, with ≥95% sensitivity. A commercial BCID Panel is available from BioFire Diagnostics, LLC. This example uses a research version of the FilmArray BCID Panel to demonstrate methods of distinguishing between true positives and environmental contamination.

Various gram-positive and gram-negative bacteria, as well as Candida yeast isolates were tested for assay reactivity. Mock PABC samples were prepared by spiking microorganism into a mixture of human whole blood and BD BACTEC Aerobic Plus/F blood culture medium. Microorganisms were spiked at concentrations consistent with that observed for blood culture bottles that had recently been indicated 'positive' for growth by the BD BACTEC 9050 system (103 to 108 CFU/mL)(Becton Dickinson, Franklin Lakes, N.J.). Exclusivity samples were prepared at microorganism concentrations expected for blood culture bottles that may have remained overnight (~8 hours after the initial positive signal) in a blood culture machine (108 CFU/mL yeast and 1010 CFU/mL for bacteria). Samples were loaded into a FilmArray BCID pouch and processed in a FilmArray instrument. Nucleic acid extraction, purification, amplification, and results analysis are automated using the FilmArray system, with a total processing time of approximately one hour.

PABC samples from children and adults from three different sites were tested in a FilmArray BCID pouch. FilmArray results were compared to conventional blood culture and susceptibility testing. One 250 µl aliquot from each PABC was mixed with 500 µl lysis buffer, and 300 µl of this mixture was loaded into a pouch per instructions and tested for gram positive and gram negative bacteria, fungi and antibiotic resistance genes.

Within the FilmArray instrument, subsequent to sample prep, the first-stage multiplex PCR mixture was thermocycled in blister 564 from 60° C. for 25 seconds to 96° C. for 4 seconds for 20 cycles. After first-stage PCR was complete, the mixture was diluted and was transferred to each of the second-stage wells 582. The second-stage PCR reactions were subjected to 63° C. for 19 seconds to 94° C. for 0 seconds for an additional 32 cycles. Melts in this illustrative example were performed after cycles 20, 26, and 32 for each second-stage reaction well 582 to generate melting curves, and each well was called positive if the melting curve showed a melt peak (negative first derivative of the melting curve) in a pre-defined temperature range for each second-stage assay. It is noted that other cycles may be used for melt analysis, with 20, 26, and 32 cycles being illustrative only, and each assay may have its own pre-defined temperature range that is related to the Tm of the expected amplicon. The pre-defined temperature range works to exclude amplified products that are non-specific, such as primer-dimers, which often will have a significantly different Tm. For organisms with variability in the target sequence, it may be desirable to have a wider pre-defined range, as sequence variability may result in slightly different Tms. For organisms with highly conserved target sequences, it may be desirable to have a narrower pre-defined temperature range, thus excluding most non-specific and cross-reactive amplification.

FIGS. 5A-B show illustrative amplification and melting results for an *A. baumannii* test. FIG. 5A shows results for a contaminant that could lead to a false positive call, while FIG. 5B shows the results for a true positive that was run after blood culture, as discussed above. It is noted that each assay is run in triplicate in high density array 581 in the illustrative BCID Panel, and two of the three wells 582 must show a positive result for the system to call that organism positive. In FIG. 5A, in two of the three replicates the amplification curve shows a crossing point ("Cp") of 29.2. Thus, a call made before cycle 29, illustratively at cycles 20 or 26, would be negative, but a call made after cycle 29, illustratively at cycle 32, would be positive. This is confirmed in the melts, where there is no melt peak after cycles 20 (melt 1) and 26 (melt 2), but there is a clear melt peak after cycle 32 (melt 3) for all three replicates, using a pre-defined temperature range of 78-83° C. Using either the amplification curve or the melt peaks, with the illustrative 20 or 26 second-stage amplification cycles, this assay properly could have been called negative, but if PCR had gone through the illustrative 32 cycles, this assay could have resulted in a false positive. In FIG. 5B, it is seen that the true positive amplified much earlier, with a Cp between 7.9 and 8.0 for each well, and melt peaks at all three illustrative cycles would be called positive.

From FIGS. 5A-B, one may consider terminating the second-stage amplification at a cycle no later than cycle 26. Indeed, if A. baumannii were the only organism assayed, such would be a good strategy. However, a number of organisms in the BCID Panel and in other panels amplify much later, illustratively because of slower growth in culture, less efficient PCR, or because there are fewer copies of the target sequence in a positive blood culture. Fewer copies of the target sequence may be present because the organism is capable of triggering a positive blood culture with fewer cells, or because there may be only one copy of the target sequence per cell, as compared to plasmid or RNA sequences that may be present in significantly higher copy numbers.

FIGS. 6A-B show illustrative amplification and melting results for a C. tropicalis assay. With this organism, true positives often do not show up until after cycle 26. With *C. tropicalis*, false positives would be rare, but false negatives would be common if second-stage PCR were terminated significantly earlier than cycle 32. If a single second-stage cycle were chosen for all assays, there would be either a risk of false positives for the assays that tend to have an earlier Cp (such as *A. baumannii*) or a risk of false negatives for assays that tend to have a later Cp (such as *C. tropicalis*), or both if a compromise cycle were chosen. Using different cycles for the calls for each of these organisms improves the overall accuracy of the assay.

Figure 7B:
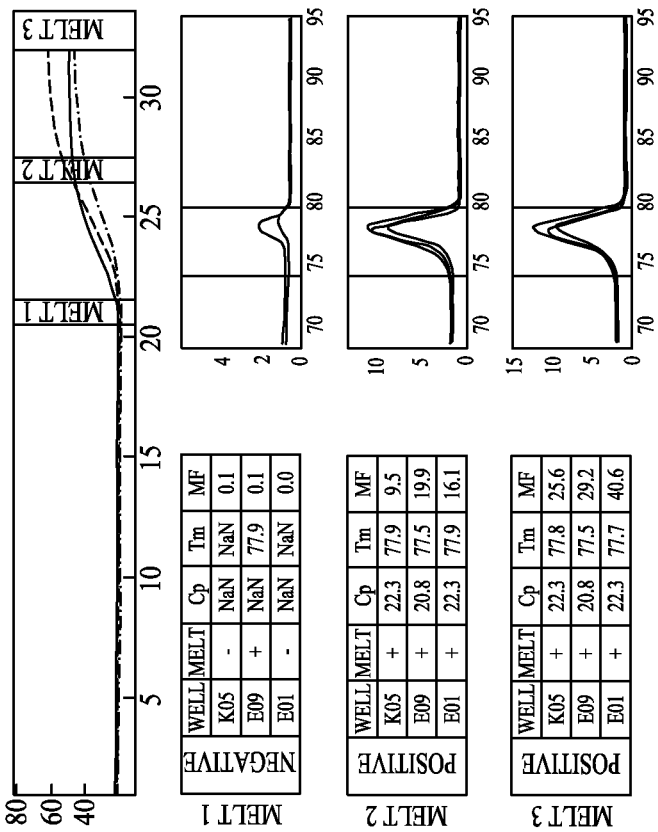
FIGS. 7A-B show amplification and melting curves after three different cycles for S. aureus.
Figure 7A:
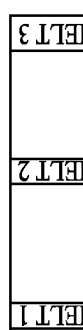
Figure 7A:
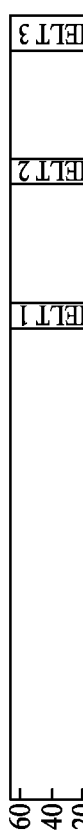

FIGS. 7A-B show the amplification and melting results for an *S. aureus* assay. With this organism in the FilmArray BCID Panel, true positives sometimes show up as early as cycle 20. FIG. 7B shows that all three replicates were called negative after 20 cycles by Cp, but one replicate was called positive by melt. However, all three replicates were called positive after 26 cycles by Cp and melt. While the true negative shown in FIG. 7A did not show any amplification, even after 32 cycles, it is known that S. aureus is a moderate contamination risk. Accordingly, while choosing cycle 32 may be acceptable based on the data shown in FIGS. 7A-B, cycle 26 is also a viable choice, with less risk of false positives from environmental contamination.

Each organism in the illustrative BCID Panel was analyzed to determine whether melt cycle 1 (second-stage PCR cycle 20), melt cycle 2 (second-stage PCR cycle 26), or melt cycle 3 (second-stage PCR cycle 32) would be most appropriate to use to minimize both false positives and false negatives. The organisms were assigned as follows in Table 1:

TABLE 1

| Melt Cycle 1 (Cycle 20) | Melt Cycle 2 (Cycle 26) | | Melt Cycle 3 (Cycle 32) |
| --- | --- | --- | --- |
| A. baumannii | Enterococcus | K. pneumoniae | C. albicans |
| E. coli | L. monocytogenes | K. oxytoca | C. glabrata |
| E. cloacae | Staphylococcus | S. marcescens | C. krusei |
| Enterobacteriaceae | S. aureus | P. aeruginosa | C. parapsilosis |
| Proteus | Streptococcus | N. meningitidis | C. tropicalis |
| | S. agalactiae | mecA | |
| | S. pneumoniae | KPC | |
| | S. pyogenes | vanA/B | |
| | H. influenzae | | |

In the illustrative embodiment, the FilmArray instrument was programmed to collect the melt result for each organism only in the melt cycle listed above. While only the melt cycle identified in Table 1 was used for each organism, it is understood that obtaining amplification or melt peak information over multiple cycles for a single well may be useful in some circumstances.

In general, melt cycle 1 targets are present at the highest titers in positive aerobic blood cultures, but also present as background organisms and are the highest risk for unexpected positives. Melt cycle 2 targets present at high titers in positive aerobic blood cultures, but have a low presence as background organisms and are a medium risk for unexpected positives. Melt cycle 3 targets present at low titers in positive aerobic blood cultures, but also have low to no presence as background organisms and have a low risk for unexpected positives.

When the three melts discussed above were used, it was found that the illustrative version of the FilmArray BCID Panel exhibited 100% reactivity (111/111) with the panel of inclusivity microorganisms (including those harboring antimicrobial resistance genes). For example, the illustrative FilmArray BCID Panel detected 17/17 *Staphylococcus* isolates, 19/19 *Enterococcus* isolates, and 30/30 Enterobacteriaceae isolates. Similarly, the illustrative FilmArray BCID system did not detect 62/62 (100%) microorganisms for which the assays were not expected to react. The average specificity per interpretation [True Negative/(True Negative+False Positive)] in the BCID system was 100% (155/155; 95% CI 98.1-100.0%). These results demonstrate that each well may be called correctly using only a single melt cycle for that reaction, which may be different than the single melt cycle used for the reaction in another well in the same assay.

While three melt cycles were used in this example, it is understood that any number of melt cycles may be used and that any cycle may be chosen as a melt cycle. Separation between false positives and false negatives may be achieved with only two melt cycles in some assays, whereas four or more melt cycles may be needed in other assays. Further, while the example used samples from culture, it is understood that multiple melt cycles may be appropriate for assays using uncultured materials. Further, while melting is used in this example, amplification curves with cut-offs or Cps at the various cycles may be used to determine whether the sample is positive for the target.

Additionally, it is understood that the information obtained for one organism can be used to assist with positive or negative calls for other organisms, particularly if there is some cross-reactivity between the organisms, or if there is some other relationship between the targets, such as a bacterium and an antibiotic resistance gene associated with that bacterium. In the above example, *Enterococcus* ("Entero") and *Staphylococcus* ("Staph") are both detected in melt cycle 2. However, in many known assays for Entero, due to similarities in target sequence, there is cross-reactivity with Staph, thereby potentially causing a late Cp in a true negative Entero sample that is positive for Staph. To reduce the effect of potential cross-reactivity for the Entero assay in such a situation where cross-reactivity is an issue, a positive or negative call for Staph may be made, illustratively using melt cycle 2 (cycle 26). If Staph is positive, thereby affecting the Entero sample, Entero could be called based on an earlier result, illustratively melt cycle 1 (cycle 20). If Staph is negative, then the Entero assay would be unaffected and the call may be made illustratively at melt cycle 2, or whichever cycle was chosen as optimized for that assay without cross-reactivity. It is noted, however, that in blood culture, a positive bottle ring is based on the combined organism growth of all organisms that are present, and one or more organisms may be present at amounts lower than either would be from a single infection. The cycle at which the cross-reactive assay is called may need to be adjusted accordingly. By adjusting the cycle used for the call of the cross-reactive assay based on a positive or negative call from the other assay, cross-reactivity issues from double infection samples can be called accurately, illustratively without the need to redesign the primers to avoid cross-amplification.

It is understood that, while the above example identifies organisms, it is understood that the same methods and devices may be used to identify different target sequences in one or several organisms by amplifying different loci of that organism.

EXAMPLE 2

In Example 1, melting curves acquired at different cycle numbers were used to distinguish between environmental contamination and clinical infection, wherein each test in the panel was assigned a cycle number, and positives and negatives were called based on the result at the assigned cycle number. Using different cycle numbers for calls can also be used to distinguish between potential "false positives" where nucleic acid is present at substantial quantities but not clinically relevant and clinically relevant true positives that do not have a crossing point until a later cycle. One such example is with latent viral infection through chromosomal integration, wherein the chromosomally integrated viral DNA may or may not be responsible for the clinical symptoms.

For example, an individual may have inherited the HHV6 virus from a parent who had been infected with the virus and the virus was latently chromosomally integrated (termed chromosomally-integrated HHV6, "ciHHV6"). This individual would have some or all of the HHV6 virus integrated in essentially every nucleated cell, and a PCR test for HHV6 would always come up positive, even if the individual has a latent infection with no active clinical symptoms from that virus. For such a patient with no active symptoms from that virus, the integrated viral chromosome would not be clinically relevant, and any symptoms would be from some other source.

For HHV6 patients who have an active case of meningitis and do not have ciHHV6 virus (hereinafter "clinically-relevant infection"), it is expected that a FilmArray second-stage crossing point from a spinal fluid sample would be around cycle 25-30, while a meningitis patient having a latent ciHHV6 virus would have a FilmArray second-stage crossing point around cycle 6-10. In such a situation, the first melt cycle could be illustratively around cycle 10, and a later melt cycle could be done illustratively around cycle 30. However, it is understood that these cycles are illustrative only and other cycles may be appropriate. If the first melt cycle were positive, the test may report a "negative", or it may report a "chromosomal integration" or some other result indicative of the early cycle positive result. Of course, if the first melt cycle were positive, the later melt cycle would also be positive. However, if the first melt cycle were negative and the second melt cycle were positive, this would be an indication of current infection, and a "positive" result would be reported. Thus, in some cases, an early cycle "positive" can be used to identify a non-clinically relevant positive result.

EXAMPLE 3

In Examples 1 and 2, different cycle numbers were used to distinguish between environmental contamination, potentially non-clinically relevant infection, and clinically-relevant infection. In this example, additional cycles are used to enable detection of low level true positives. In this method, the detection and identification method is a modified two-step process. The first step is a set amplification protocol, optionally with additional melt cycles as used in Examples 1 and 2, and the second step employs a higher signal-to-noise detection during at least one subsequent melt. An illustrative protocol is shown in FIG. 8.

Figure 8:
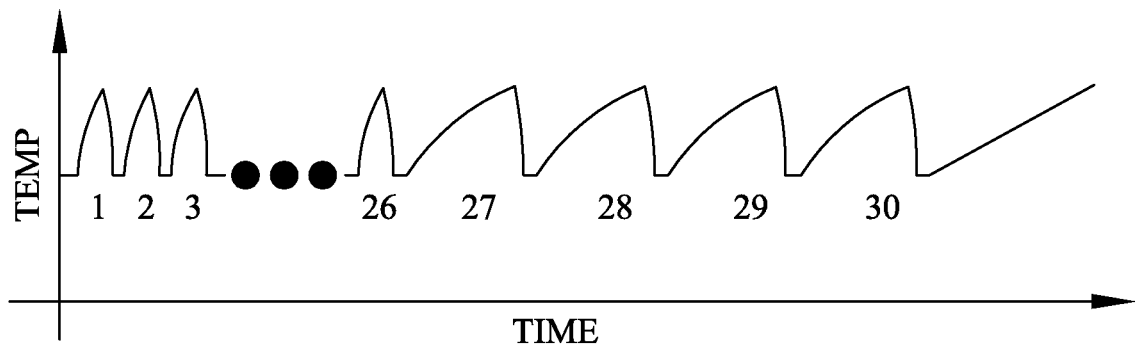
FIG. 8 shows an illustrative cycling protocol for detecting low load samples.
Figure 9:
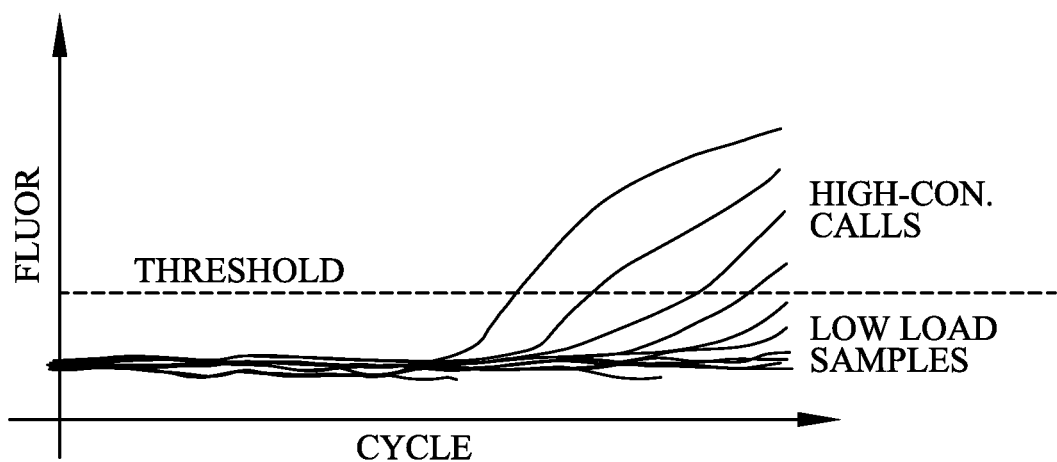
FIG. 9 shows illustrative amplification curves and cut-off fluorescent threshold.

As shown in FIG. 8, a set number of amplification cycles, illustratively 26 cycles, are run. Any wells that return a positive result at cycle 26 optionally need not be analyzed further. The positive result may be made by amplification curve, or may be made or confirmed by a melting curve analysis as discussed above, for those samples that show amplification, illustratively by exceeding a threshold fluorescence level as indicated by the High-Con calls in FIG. 9, or other methods as are known in the art. Thereafter, optionally a melt is run during each of a plurality of additional cycles. After each cycle, if a melt peak is detected, the shape of the amplification curve optionally may be analyzed for further confidence of the positive calls. Illustrative methods of making positive calls from the shape of amplification curves may be found in U.S. Pat. Nos. 6,387,621; 6,730,501; 7,373,253; and 9,273,346, all of which are herein incorporated by reference. Such methods may aid in distinguishing true amplification from signal drift, which is particularly useful with low level positives. After these additional cycles, illustratively after cycle 30, the light source, illustratively an LED although other excitation devices may be used, in the instrument is adjusted to increase the power. After adjusting the LED power, the instrument collects fluorescence data during a melt. This power adjustment is made to increase the signal-to-noise ratio for detecting low load samples. A reason for not going to full power for the initial melt is that this may have the effect of railing the signal from one or more sample wells that were called positive after cycle 26, as these samples already had a significant load. However, data collection from these wells optionally would be terminated after the positive call at cycle 26, so the railing would not have any effect on reported results. Finally, a melting curve analysis (amplification detection as described above and/or and Tm identification) is performed on all reactions with a cycle 26 or cycle 30 end-point fluorescence less than the established threshold, to determine whether any of these sample wells contain a true positive result.

It is understood that the use of cycles 26 and 30 is illustrative only, and that other cycles may be used, as may be desired for the specific application. Furthermore, the additional cycles 27-30 may be omitted, and the light source may be adjusted after the initial amplification.

EXAMPLE 4

Optionally, instead of or in addition to multiple melting cycles, the light source in the instrument, illustratively an LED, although other excitation devices may be used, may be adjusted for different assays. The data in Table 2 show that if the LED power is reduced, thereby reducing the fluorescence signal, the detection of background bacterial organisms can be reduced. In one illustrative example, reducing the LED power from 70% (approximate current FA setting) to 50% reduced unexpected false positive detection by the FA BCID Enterobacteriaceae test from 90% to 20% of tests after 32 cycles.

TABLE 2

| FA BCID Assay | 10% LED Power | 30% LED Power | 50% LED Power | 70% LED Power | 90% LED Power | Historical Background detection (65% LED Power) |
|---|---|---|---|---|---|---|
| Abaumannii | 0/10 (0%) | 1/10 (10%) | 0/10 (0%) | 0/10 (0%) | 0/10 (0%) | 2.17% |
| Ecloacae | 0/10 (0%) | 0/10 (0%) | 0/10 (0%) | 0/10 (0%) | 0/10 (0%) | 8.70% |

TABLE 2-continued

| FA BCID Assay | 10% LED Power | 30% LED Power | 50% LED Power | 70% LED Power | 90% LED Power | Historical Background detection (65% LED Power) |
|---|---|---|---|---|---|---|
| Ecoli | 0/10 (0%) | 0/10 (0%) | 0/10 (0%) | 4/10 (40%) | 5/10 (50%) | 23.40% |
| Enterobacteriaceae | 0/10 (0%) | 5/10 (50%) | 2/10 (20%) | 9/10 (90%) | 10/10 (10%) | 78.72% |
| mecA | 0/10 (0%) | 0/10 (0%) | 2/10 (20%) | 0/10 (0%) | 0/10 (0%) | 22.58% |

While an illustrative setting is 70% LED power, a single setting may or may not be appropriate for all assays, and it is understood that the ideal LED power may be different for various assays within an array or panel. For example, an assay that is more susceptible to false positives from environmental contamination may be better off with a lower power setting to reduce sensitivity, while an assay that for which low-level positives are important may benefit from higher LED power. Thus, after the individual positive or negative calls are made, the LED power may be reduced, illustratively by 5%, 10%, 15% or more or any other level, and a melting curve generated. If the melting curve is negative, that assay may be flagged as a potential false positive, or it may be reported as a negative. Alternatively or additionally, the LED power may be increased, illustratively by 5%, 10%, 15% or more or any other level, and assays that were previously called negative may be interrogated, with subsequent melting curves potentially indicated a positive result for a low-level assay.

While LEDs and LED power is discussed herein, it is understood that other illumination sources may be used, including incandescent, fluorescent, and other lamps, and adjustment of the power and concomitant lighting output of such lamps is also within the scope of this invention.

EXAMPLE 5

Figure 10:
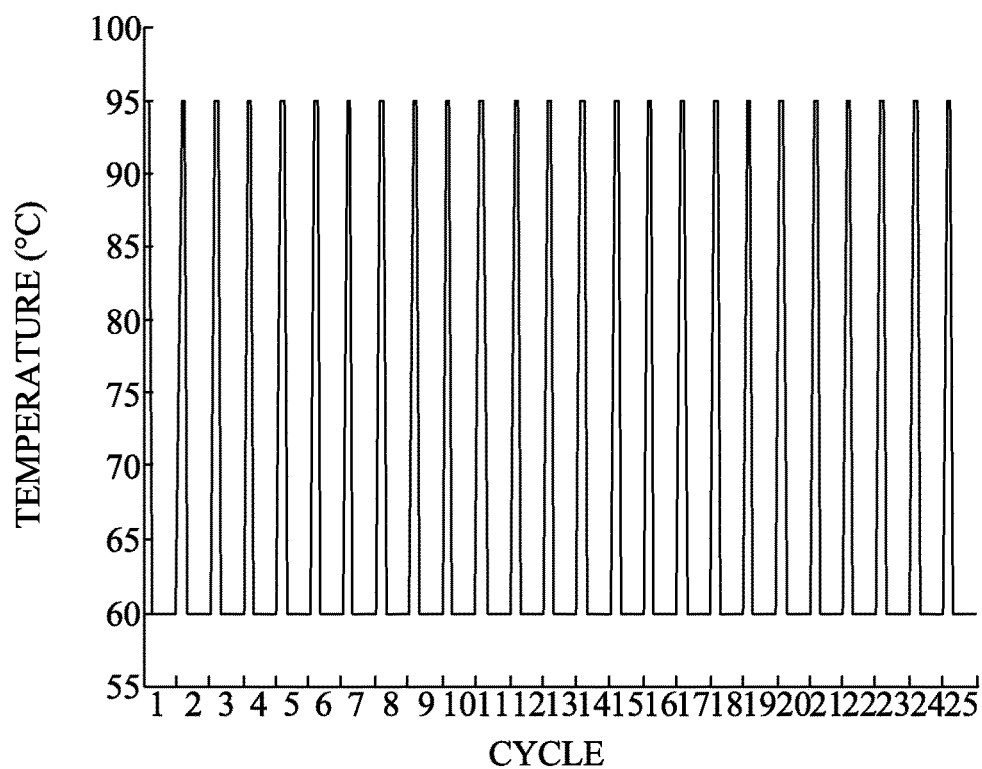
FIG. 10 shows illustrative temperature data that may be collected during a typical two-step PCR protocol. During the denaturation/annealing segment, the temperature is increased from the baseline value to the maximum, followed by a decrease in temperature back to the baseline. During the extension segment, the temperature is held constant.

As an extension of the previous examples, melting curves may be acquired during additional cycles, for example at every cycle or nearly every cycle of PCR, illustratively through continuously acquired temperature and fluorescence data during amplification. For example, an illustrative two-step PCR protocol may be divided two segments: a denaturation/annealing segment where the temperature is constantly changing, and an extension segment where the temperature is held constant. During the denaturation/annealing segment, the temperature of the PCR reaction is increased, illustratively at a constant rate, from a baseline value to a maximum temperature value, followed by a rapid decrease in the temperature back to the baseline value. As the temperature is increased, the dsDNA is separated into two ssDNA fragments. As the temperature is decreased, the PCR primers anneal to the two ssDNA fragments. During the extension segment, the temperature is held constant at the baseline value, allowing the primed ssDNA fragments to extend to form two dsDNA fragments. FIG. 10 is a graphical depiction of this illustrative temperature cycling protocol. However, it is understood that other protocols may be used, wherein the temperature is held constant at any or all of the melting temperature, the annealing temperature, and the elongation temperature, or without any holds. Also, it is understood that the baseline annealing temperature may be the same as or different from the extension temperature.

Figure 11:
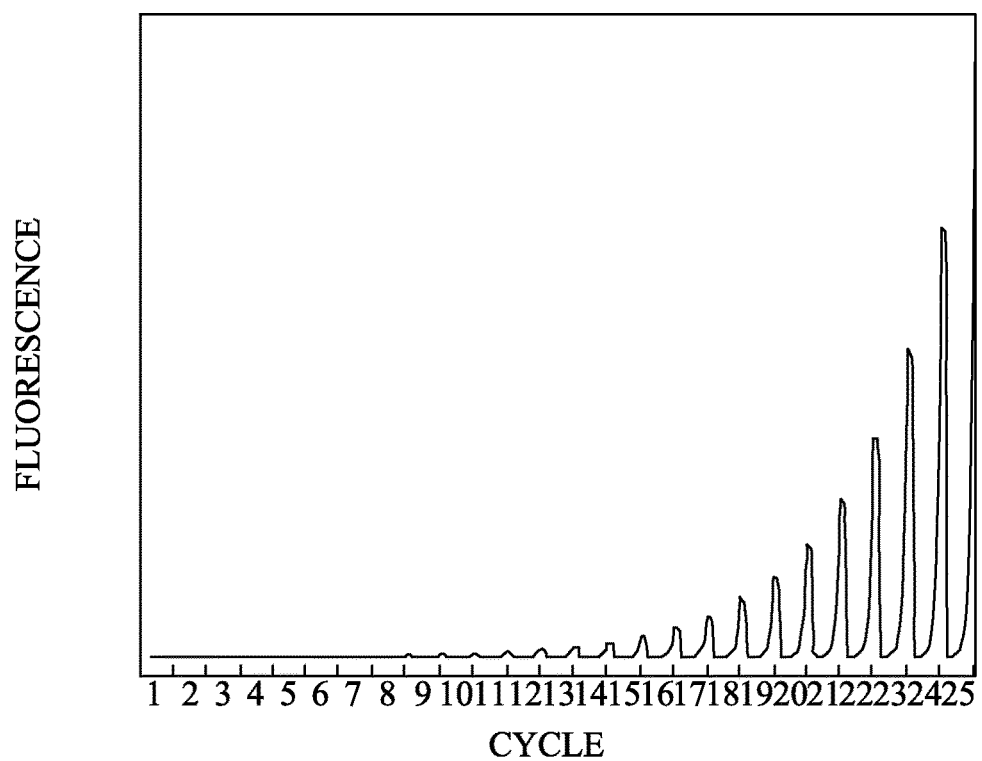
FIG. 11 shows illustrative continuous monitoring of fluorescence data that may be collected during the two-step PCR protocol of FIG. 10.
Figure 12:
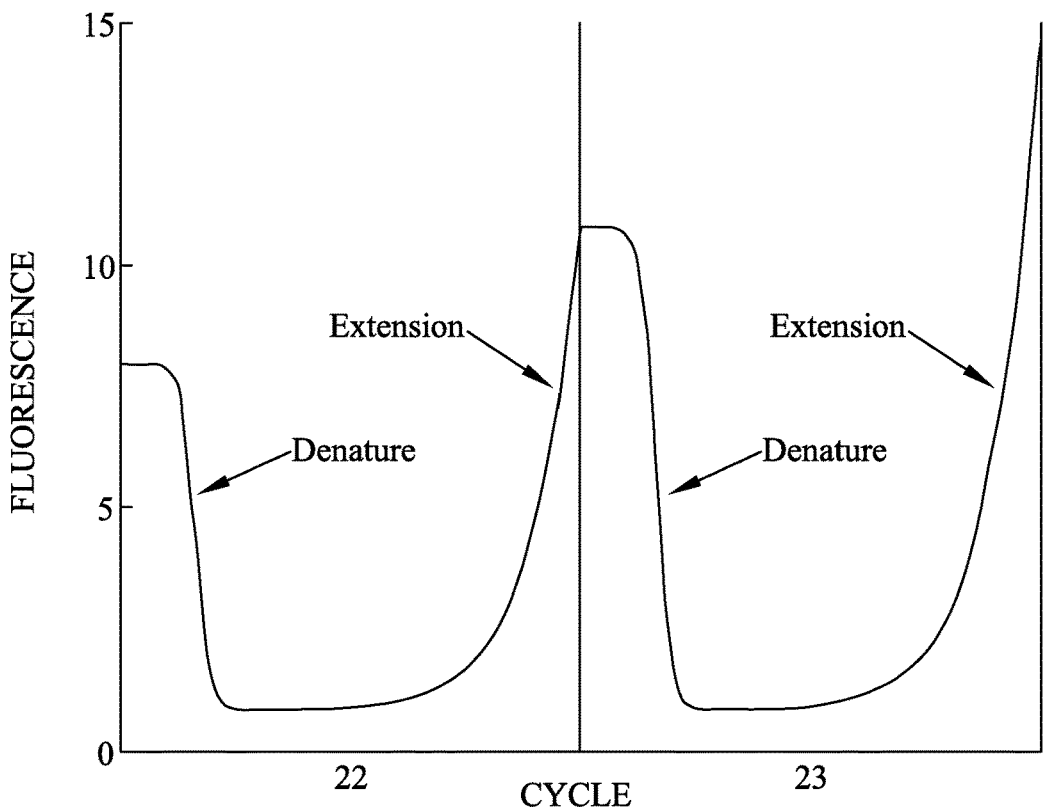
FIG. 12 shows illustrative continuous monitoring of fluorescence data that may be collected during two cycles of a typical two-step PCR protocol. During the denaturation segment, the fluorescence data decreases as the saturating dsDNA-binding dye is released from the dsDNA, resembling a typical melting curve. During the extension segment, the fluorescence data increases as the primed ssDNA fragments are primed and extended into dsDNA fragments.
Figure 13:
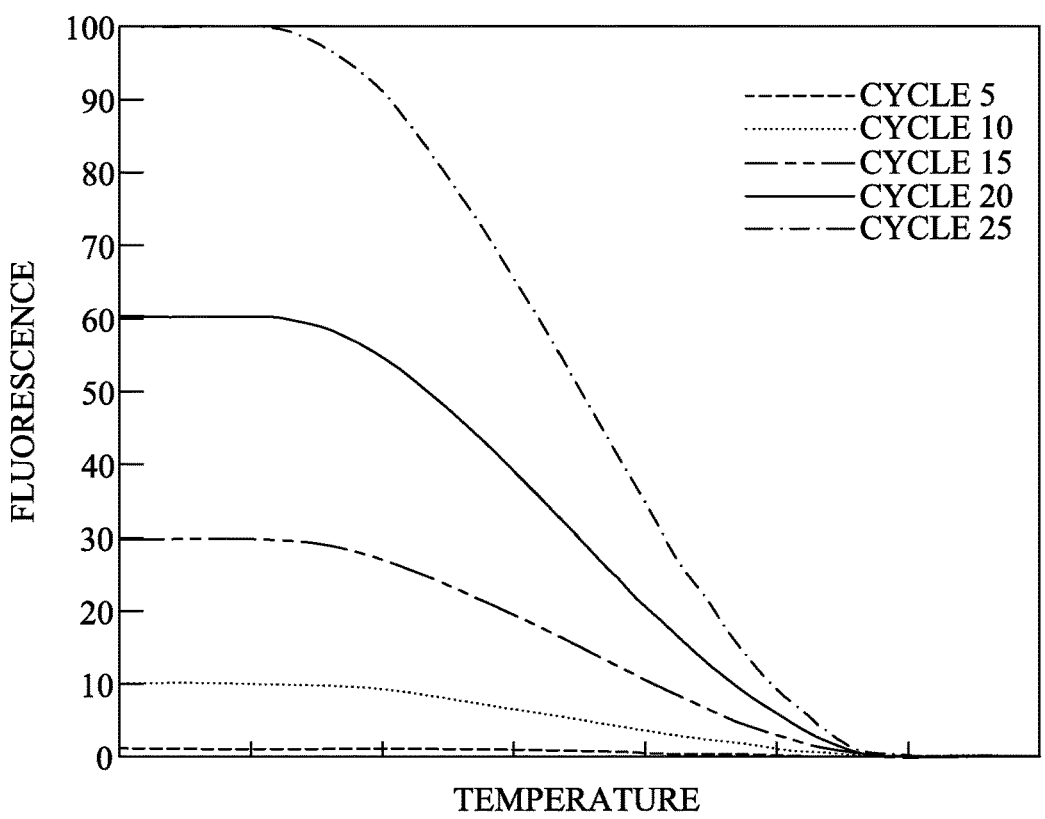
FIG. 13 shows an overlay of illustrative fluorescence data that may be collected during the denaturation segments for several cycles of PCR.

With continuous data acquisition, an instrument may collect temperature and fluorescence data during both segments of the PCR protocol, continuously for all cycles, as shown in FIG. 11. Fluorescence data collected as part of the denaturation segments can be thought of as a series of melting curves. In between each melting curve, the fluorescence data shows amplification as the PCR product is extended and non-specific dsDNA-binding dyes may be used to detect the amplification product (see FIG. 12). At the start of PCR cycling, the amount of dsDNA is low and, therefore, the signal generated during the denaturation segment, is also low. As cycling continues, the amount of PCR product begins to increase. Similarly, the signal generated by the denaturation segment also increases. See FIG. 10 for a graphical depiction of the change to melting curves as PCR cycling progresses and FIG. 13 for a series of melting curves during multiple cycles.

Figure 14:
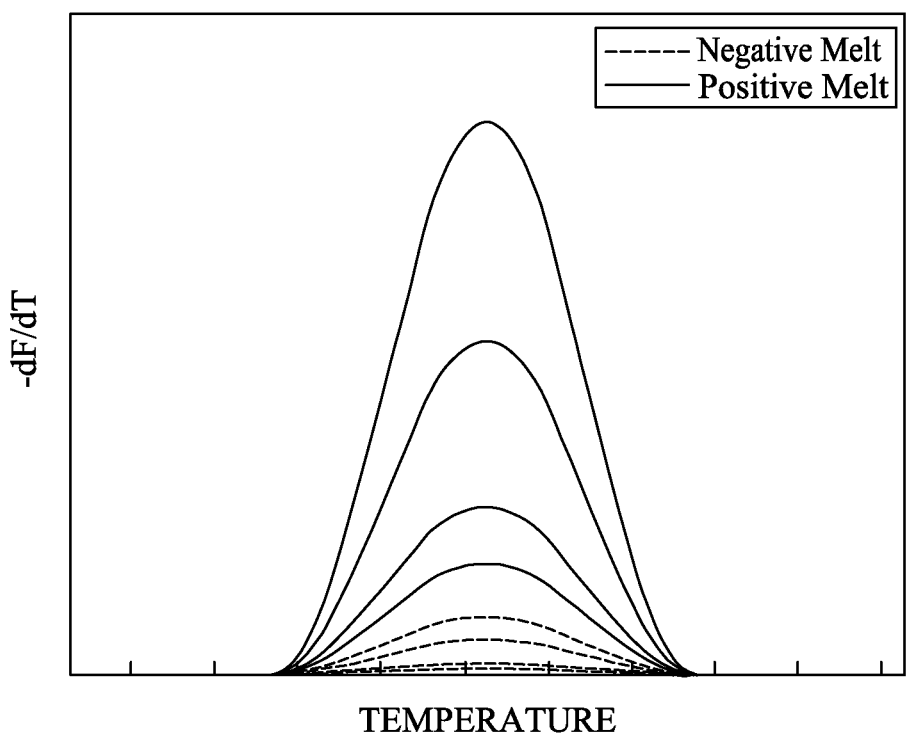
FIG. 14 shows an overlay of illustrative the negative first derivative of the fluorescence data collected during the denaturation segments for several cycles of PCR.

One method for quantifying a target nucleic acid is by determining Cp and comparing the Cp to a standard or to a control. As an alternative to determining Cp by absolute or normalized amplification data, the series of melting curves discussed above may be used. FIG. 14 shows an illustrative set of negative derivative melting curves, wherein the flattest curves represent the earliest cycles and the area under the curve increases through a number of cycles. It is expected that such derivative melting curves acquired at a plurality of cycles during amplification can be used to determine Cp. In this illustrative example, the height of the transition for each melting curve or the area under the negative first derivative of the melting curve can be determined for each cycle. The Cp may then be assigned to the cycle at which this value exceeds a pre-determined threshold. It is understood that every cycle may be used, or fewer than all cycles may be used for an approximate Cp.

Additional methods for determining Cp may be applied. For example, a melt detector may be used (see U.S. Pat. Nos. 6,387,621; 6,730,501; and 7,373,253, herein incorporated by reference). The detector would interrogate curve shape and background noise to determine if PCR product is present in the sample. The use of a melt detector could be used to increase the sensitivity of the system (See Poritz, et al., PLos One 6(10): e26047). Optionally, additional filters could be applied to the melting curve analysis to window the melt transition to increase the specificity of the system, by analyzing only those melting curves having a melting transition, illustratively displayed as a melt peak, within a set temperature range. It is expected that such methods would result in a more accurate Cp.

EXAMPLE 6

In another illustrative example, methods of continuous monitoring of temperature and fluorescence are used for relative quantification, illustratively using a dsDNA-binding dye in a single reaction with a control nucleic acid. In this example, a multiplexed PCR reaction is provided, containing a control nucleic acid at a known initial concentration and a target nucleic acid at an unknown concentration. Illustratively, primers for amplification of the control nucleic acid are present at the same initial concentration as primers for amplification of the target nucleic acid. In addition, it is desirable if the control nucleic acid is selected such that its melting temperature is sufficiently well separated from the melting temperature of the target nucleic acid, so that melting of each of these nucleic acids is discernable from melting of the other. It is understood that multiple target nucleic acids of unknown concentration may be multiplexed in the reaction, noting that it is desirable that the melting curve for each nucleic acid is distinguishable from the others and from the control nucleic acid.

Figure 15:
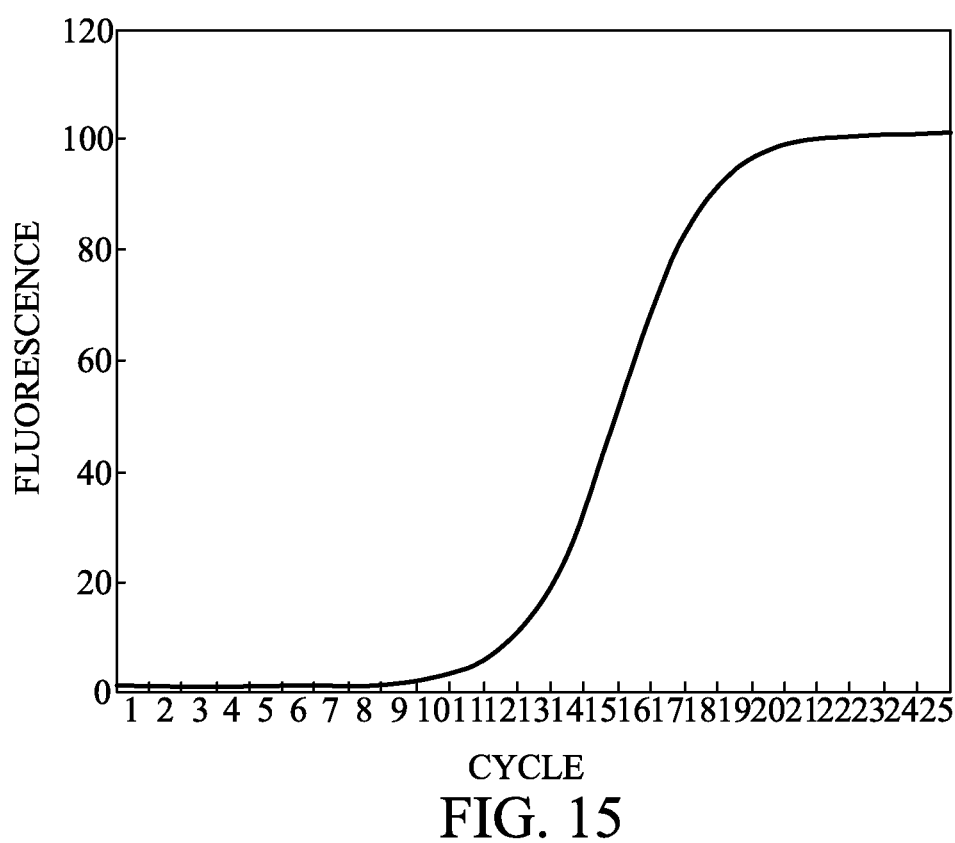
FIG. 15 shows a typical amplification curve for a multiplexed PCR reaction that includes a control nucleic acid and a target nucleic acid of unknown concentration.

In an illustrative PCR application, the amplification of the control nucleic acid and the target nucleic acid produce an amplification curve similar to that shown in FIG. 15. In such a curve generated using a dsDNA binding dye, signal from the control and the target combine to generate a single amplification curve as shown, and information about the amplification of the individual nucleic acids is not discernable.

Figure 16:
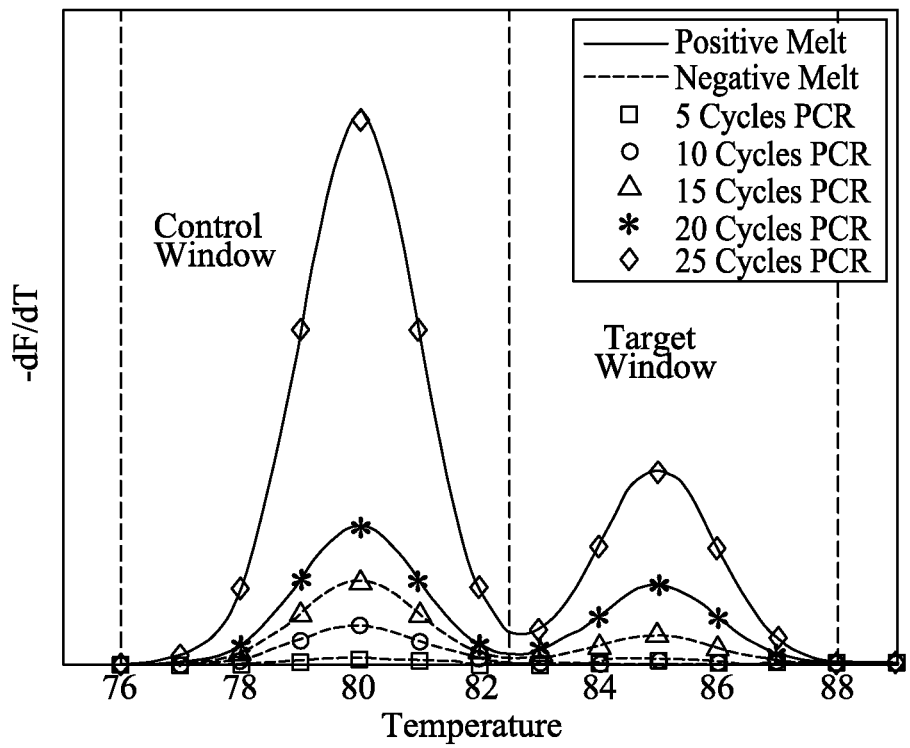
FIG. 16 shows an overlay of illustrative negative first derivative of fluorescence data that may be collected during the denaturation segments for several cycles of PCR of a multiplex reaction containing a control nucleic acid and a target nucleic acid.
Figure 17:
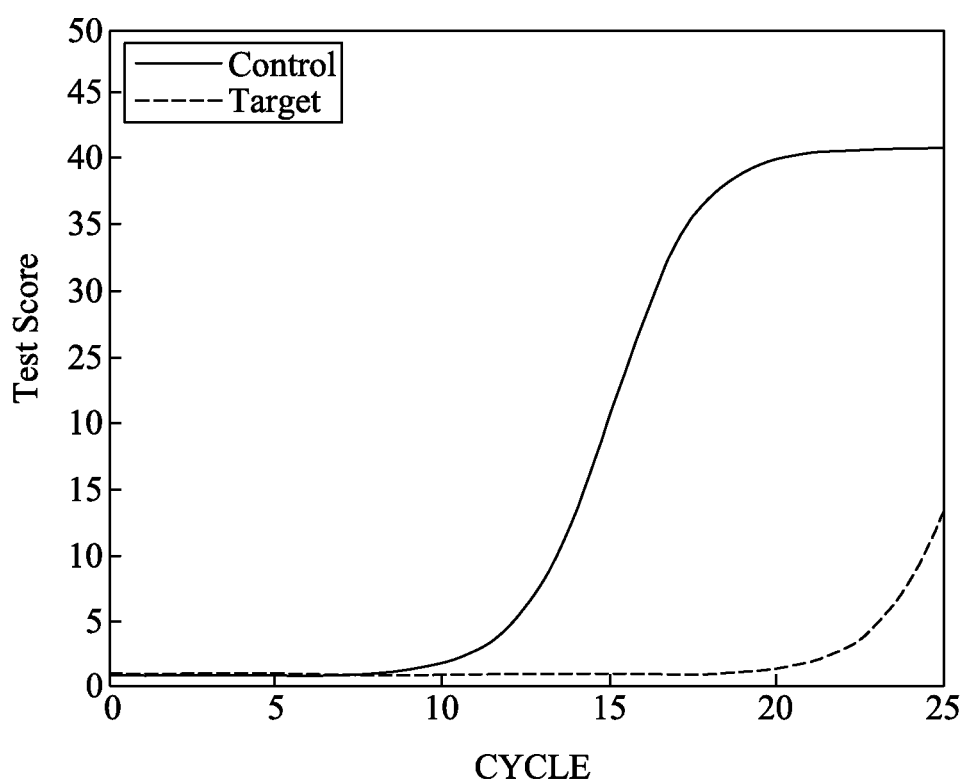
FIG. 17 shows illustrative adjusted real-time PCR curves for the control and sample nucleic acids of FIG. 16. By integrating the negative first derivative of the melting curves generated by continuous monitoring the PCR reaction over the control window, an adjusted amplification curve for the control nucleic acid is generated (solid line). By integrating the negative first derivative of the melting curves generated by continuous monitoring the PCR reaction over the target window, an adjusted amplification curve for the target nucleic acid is generated (dashed line).

With continuous data acquisition, a series of melting curves are generated during PCR cycling. Provided that the melting temperatures of the control nucleic acid and the target nucleic acid are sufficiently separated, the melting profile of each of the two reactions can be distinguished, as shown in FIG. 16. Illustratively, an adjusted amplification curve for the target nucleic acid and optionally for the control nucleic acid can be generated from this series of melting curves. Illustratively, to generate a corrected amplification curve for the control nucleic acid, at each cycle the integral of the negative first derivative of the melting curve over a pre-defined melt window can be computed and plotted as a function of the cycle number, with the Cp determined as the cycle at which each value exceeds a predetermined value. Similarly, a corrected amplification curve for the target nucleic acid may be generated by integrating the negative first derivative of the melting curve over the pre-defined melt window for the target. FIG. 16 shows illustrative negative derivative melting curves for 5, 10, 15, 20, and 25 cycles, with illustrative pre-defined melt windows indicated for the two nucleic acids. Such corrected amplification curves are illustrated in FIG. 17. Other methods for converting the melting curve to a value are known in the art, illustratively using peak height of the negative first derivative. It is understood that the predetermined value should be selected according to method used.

The concentration of the target nucleic acid relative to the control nucleic acid may be computed using the formula:

Relative Concentration=$ET^*Cp,t/EC^*Cp,c$     [Equation 1]

where
    ET and EC are the target and control efficiencies, and
    Cp,t and Cp,c are the target and control crossing points.

The efficiency of the two reactions may be determined empirically and the Cp values for the two reactions may be computed using standard calculations on the amplification curves computed from the series of melting curves, as is known in the art.

EXAMPLE 7

As discussed in the above Examples, melting curves may be acquired during several different cycles. However, in a typical PCR cycle in the above examples, it takes about 10 seconds to ramp temperature from 63 to 94 degrees (about 3° C./sec) for the denaturation phase, while each of the melts in the above examples takes about 60 sec to ramp from 68 to 94 degrees (about 0.5° C./sec). Since positive and negative calls in some embodiments are made solely based on melting curve data, the higher resolution data obtained during these slower melts is desirable. However, as cycle times decrease, illustratively due to better instrumentation or chemistry, the time spent in generating the melting curves becomes an increasingly larger portion of the run time. This is particularly true for runs that include the generation of multiple melting curves, as discussed in the above Examples.

Decreasing the melting time by increasing temperature ramp rate is one solution. However, as one increases the denaturation ramp rate, the number of data points collected usually decreases, and, therefore, the quality of the melting curves tends to decrease. While such faster melting curves may be sufficient to distinguish between clear positives and clear negatives, the faster melting curves may not always have sufficient data to identify weak positives. In this example, a solution is presented that combines data collected from the denaturation phase during temperature cycling (hereinafter "in-cycle melting curves") through multiple cycles into a single composite melting curve. Illustratively, data from the last four cycles are combined, but it is understood that any two or more in-cycle melting curves may be used. This composite melting curve can provide sufficient data to make positive and negative calls, even for weak positives, or when the acquisition rate is not high enough for a high resolution melt. A composite curve may be more robust to noise and sample variance then a single curve due to combination of multiple signals. Additionally, the higher density of signal may be more favorable to an interpolation algorithm. In-cycle melting curves include temperature, fluorescence pairs. In one illustrative method, to form a composite curve, each individual curve is first normalized, for example by scaling between 0 and 1. This causes the max fluorescence value from that curve to take the value 1, and the min value to take the value 0. It is understood that other normalization methods could be used within the scope of this disclosure. Once all N curves have been normalized independently, an aggregation function may then be applied to the fluorescence, temperature pairs of all curves. This operation creates a composite curve with a higher point density than any of the individual curves, which also effectively reduces the variance that may have been experienced by any single curve. It is understood that an aggregation function refers to any algorithm that accepts multiple melt profiles as an input and generates a single output according to an assumption about the underlying data. While a smoothing spline is used as the illustrative aggregation method in the examples herein, it is understood that smoothing splines are illustrative only and that other aggregation methods may be used. Another illustrative aggregation method would be a point-by-point average of the curves. Any number of polynomial fits could be applied to each curve before averaging.

In this example, a research version of the RP2 Panel (a panel that tests for 18 viral and 4 bacterial respiratory pathogens) was used on a prototype FilmArray Torch instrument (BioFire Diagnostics, LLC). A mixture of nucleic acids for all of the targets was used as the sample, so all assays should produce a positive result. In some reactions, a high dilution of this mixture was used to emulate samples that are close to their limits of detection, with the goal of obtaining late positives (positives that have a Cp near the last cycle).

The number of fluorescent acquisitions are recorded during the denaturation phase of each cycle to generate the in-cycle melting curves.

Figure 18B:
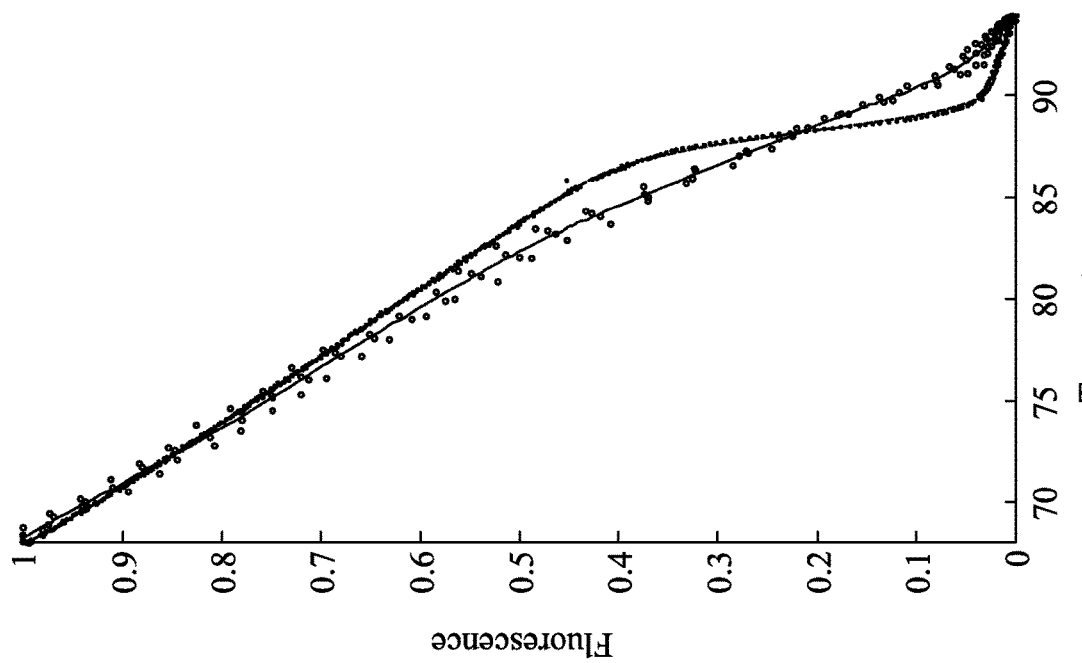
FIGS. 18A-B show fluorescence melting data acquired during a standard melt (closed circles) and during four in-cycle denaturation phases (open circles) for human metapneumovirus (FIG. 18A) and *Bordetella pertussis* (FIG. 18B).
Figure 18A:
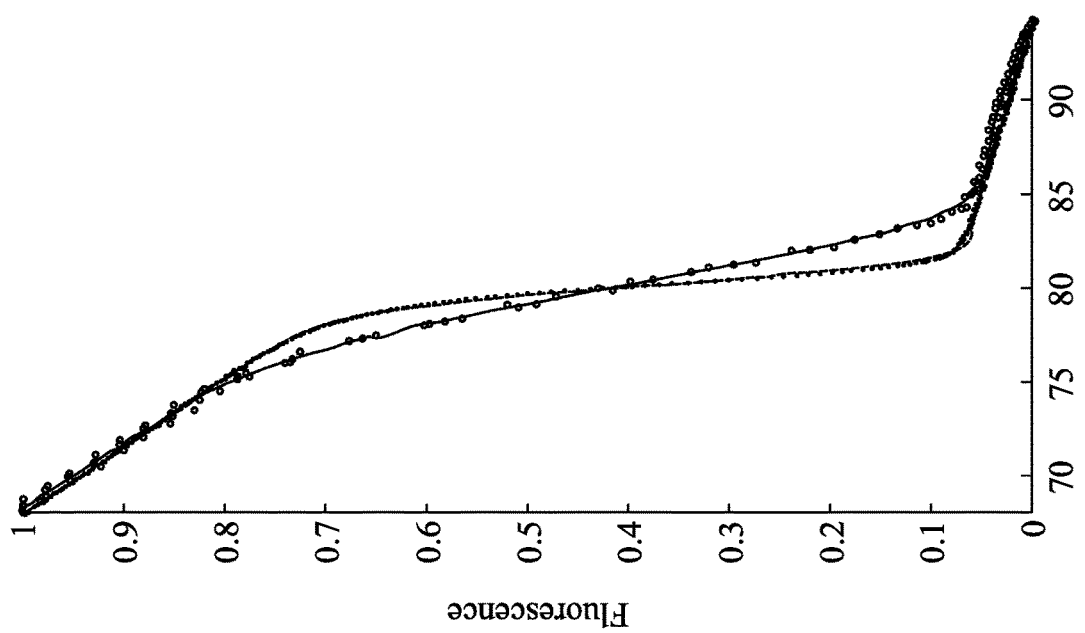

FIG. 18A shows the results for a test for human metapneumovirus (hMPV). The closed circles indicate melting curve fluorescent data acquired during a standard melt with a temperature transition of 3.0° C./sec. The open circles are melting curve fluorescent data acquired during denaturation at 7° C./sec during each of the final four cycles of PCR. The data points from all four cycles generally define a composite single melting curve (line through open circles), albeit with a slightly different curve shape from the standard melt. In these examples (as shown in FIGS. 18 and 19), the composite curve using the open circles is generated using a smoothing spline, an algorithm that attempts to fit a smooth curve to noisy data.

Figure 19B:
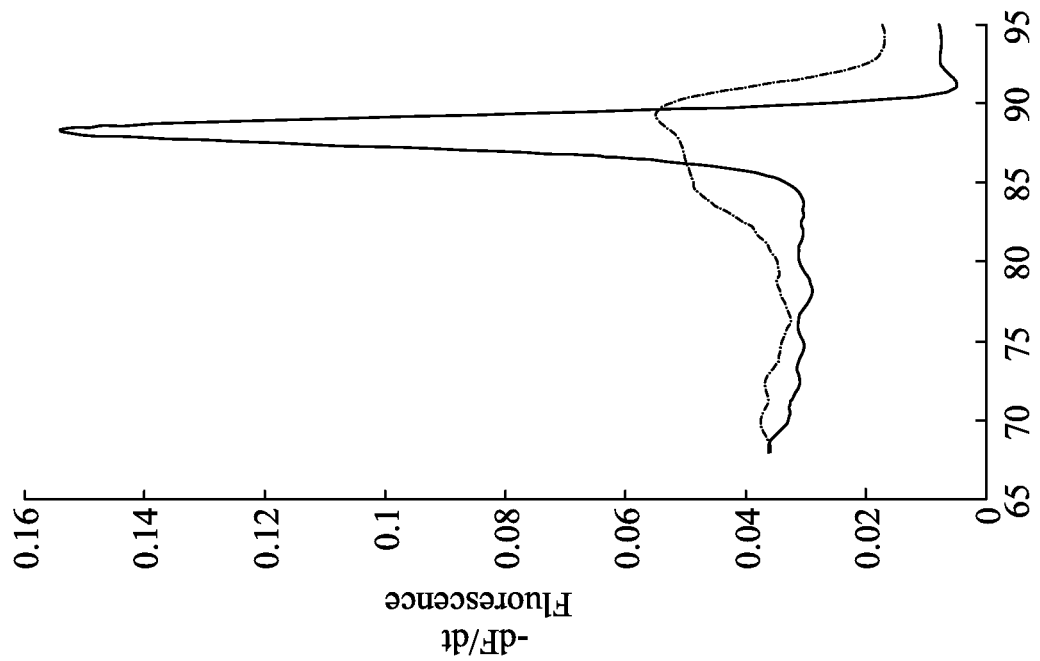
FIGS. 19A-B are derivative plots of the data shown in FIGS. 18A-B.
Figure 19A:
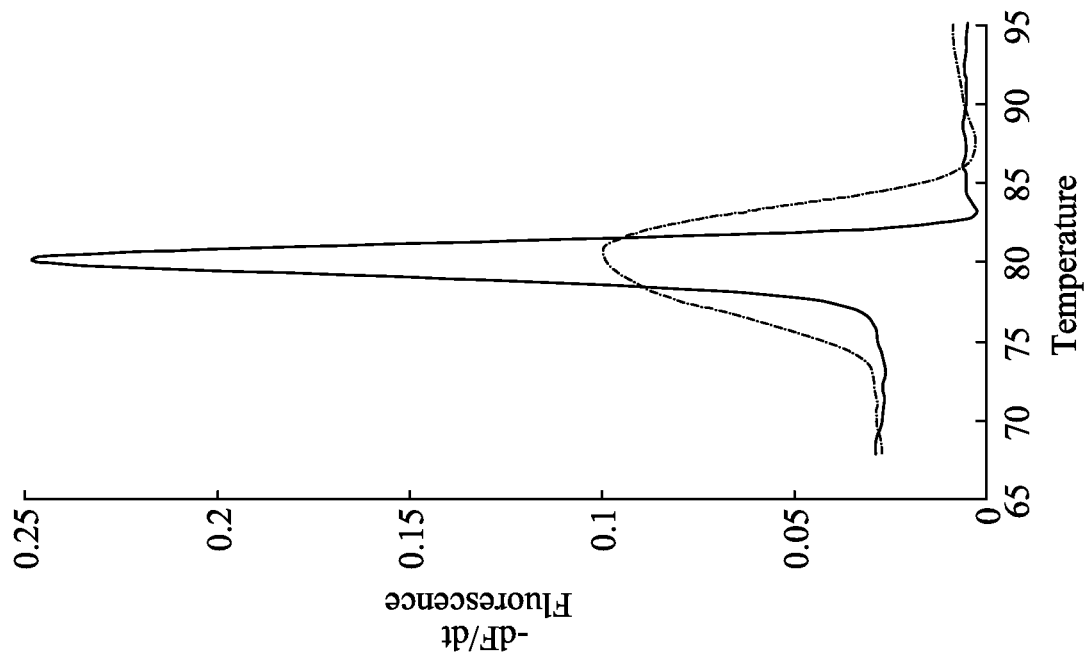

However, as can be seen in FIG. 19A, where the solid line is the derivative of the standard melt and the dashed line (-·-·-·) is the derivative of the composite curve, the two curves have essentially the same Tm and both would fall within the same melt window. With the in-cycle melting curves, it has been found that cycle-to-cycle acquisition can be off-set and the fluorescent acquisitions do not always occur at precisely the same point during temperature cycling. Thus, while melting curves from the adjacent cycles are similar, the off-set of fluorescent acquisition between cycles allows adjacent cycles to provide additional points to form a single composite curve. FIG. 18A demonstrates that it is possible to generate good melting curves using temperature transitions greater than 3° C./sec, greater than 5° C./sec, and at least up to 7° C./sec.

FIGS. 18B and 19B show similar data for a *Bordetella pertussis* assay (ptxP). However, rather than all of the in-cycle-acquired data falling on the same line (as seen by the open dots), the fluorescence data show a scattering effect around a melting curve generated by the aggregation method (FIG. 18B—composite curve through open circles). While the derivative plot did not show a single smooth melt peak, the complex peak is within the same window as the standard melt peak (FIG. 19B (-·-·-·)), and it is likely to be called positive by the melting analysis Without being bound to theory, it is expected that the different curve shape between the standard melting curves and the composite melting curve may be due to greater thermal differentiation across high density array 581 in the in-cycle denaturation, where the side next to heater 888 is warmer than the opposite side. In the slower standard melt, the sample temperature has more time to equilibrate and may be more uniform than in the faster melt. However, while the shape may be different in some embodiments, a composite melting curve generated from data collected across multiple cycles can be used to make positive and negative calls.

EXAMPLE 8

Figure 20A:
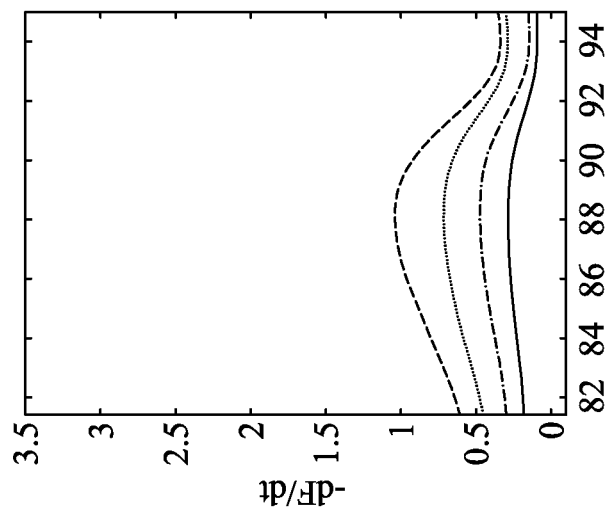

In Example 7 above, by examining an amplification curve generated during temperature cycling, it has been found that the hMPV assay had reached plateau prior to the collection of the in-cycle melting curves. Because the hMPV assay had already reached plateau, all melts were similar, all data points essentially fell on the same melting curve, as shown in FIG. 18A, and it is easy to make a positive call from this composite melting curve. By contrast, the PXTP assay had not reached plateau, and, as seen in FIG. 20A, each in-cycle melting curve had greater fluorescence than the prior in-cycle melting curve. It is believed that this increase in fluorescence causes the scattering seen in the composite melting curve shown in FIG. 18B, and may contribute to less than smooth the shape of the melt peak in FIG. 19B.

Figure 20B:
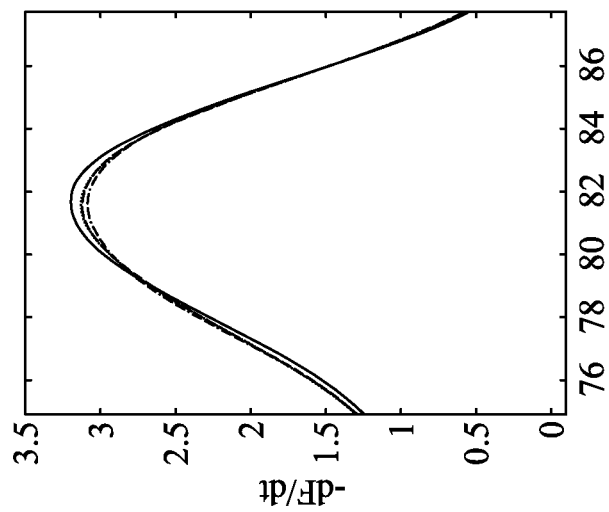
Figure 20C:
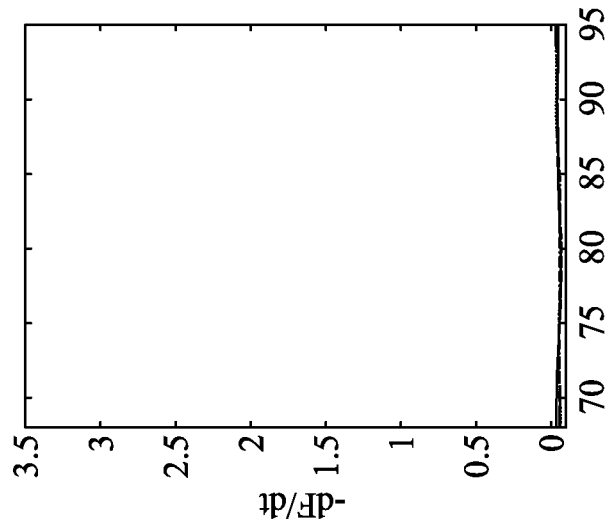

Additional information gathered from the in-cycle melting curves may be used to aid in making positive or negative calls in more difficult samples. FIGS. 20A-C show melt peaks collected during the denature ramp phase of PCR cycling for three different assays. However, unlike FIGS. 19A-B where melt peaks for the composite melting curves are shown, melting curves for each individual cycle used in making up the composite melting curves are shown. In FIGS. 20A-C, the last four cycles are shown. As discussed above, FIG. 20A shows the last four cycles for amplification of PXTP, where each cycle shows increased fluorescence over the prior cycle, presumably demonstrating that PXTP amplification continued throughout these cycles and did not plateau prior to the last cycle. FIG. 20B shows the same curves, but for a Coronavirus 229E assay. All four curves in FIG. 20B trace essentially the same line, indicating that the assay for Coronavirus 229E had reached plateau prior to the first cycle shown. It is expected that a composite melting curve for Coronavirus 229E would show a curve similar to that in FIG. 18A, with very little scattering. FIG. 20C shows the curves for a negative well, and no melt peak is exhibited.

EXAMPLE 9

One illustrative method to identify assays that are still amplifying during the cycles for which melting curves are acquired is by measuring the area under each melt peak curve. In one illustrative example, the area under the curve ("AUC") is defined by the area under the curve in a predefined melt window. FIG. 21A shows melt peaks obtained during four consecutive cycles for hMPV during another run of the RP2 Panel. In FIG. 21B, the data are replotted as melting curve vs. AUC, where the solid line represents the data from FIG. 21A, and the dashed line is the average slope. Since the hMPV assay was still amplifying, FIG. 21B shows a positive slope. To the contrary, FIGS. 21C-D show similar data for a negative assay for Middle East Respiratory Syndrome Coronavirus (MERS). The cycle melting curves do not show peaks within the melt window, and the AUC trend slope is negative. FIGS. 21E-F show similar data for an influenza B assay that plateaued after the first in-cycle melting curve. As seen in FIG. 21E, the melt peaks increased after the first cycle, but remained fairly constant through the remaining cycles. In FIG. 21F, the AUC trend line had a positive slope between cycles 1 and 2, but had a smaller slope thereafter. Illustrative factors that can be used to make positive or negative calls using in-cycle melting curves include similar curve shape, similar peak locations, and for assays that have not yet plateaued, a growing AUC. One or more of these factors may be used to make positive or negative calls. In one illustrative example, a sum of AUC above 1000 could be used as a threshold to indicate a positive melt call sample. However, it is understood that other thresholds may be used.

EXAMPLE 10

Figure 22A:
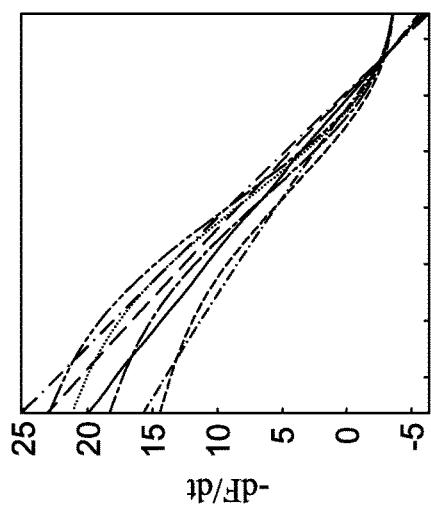
FIGS. 22A-B are similar to FIGS. 21A-B, except for Parainfluenza Virus 1.

FIG. 22A shows four in-cycle melting curves for Parainfluenza Virus 1 (PIV1). Each cycle shows increased fluorescence over the prior cycle, indicating that the assay was still amplifying. FIG. 22B shows the values of AUC for each of the four cycles, wherein, as above, the solid line represents the data from melting curves, and the dashed line is the average slope, where a clear linear trend with a positive slope indicates that the sample still amplifying during these cycles. Due to low levels of amplification, and noise present, a traditional melting call algorithm may be unable to identify the correct call. The trend in AUC suggests that given more cycles, this sample would be called positive by a traditional melting rule. In these representative examples an AUC slope larger then 20 would indicate a positive sample.

EXAMPLE 11

Figure 22C:
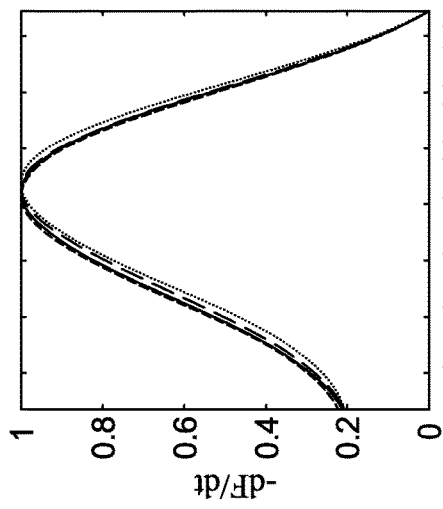
FIG. 22C is a plot of the data of FIG. 22A, except that each melt peak was individually normalized between zero and one.
Figure 22D:
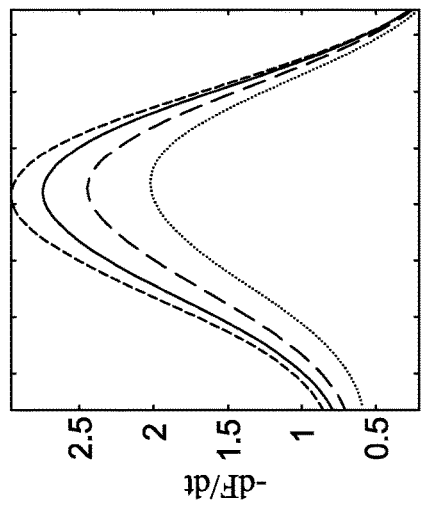
FIGS. 22D-E illustrate another approach, a polynomial fit of raw fluorescence, similar to the observation of change of AUC as in FIGS. 21A-F.
Figure 22E:
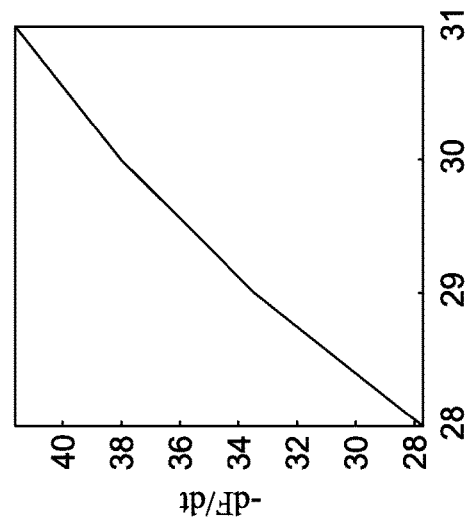
Figure 22B:
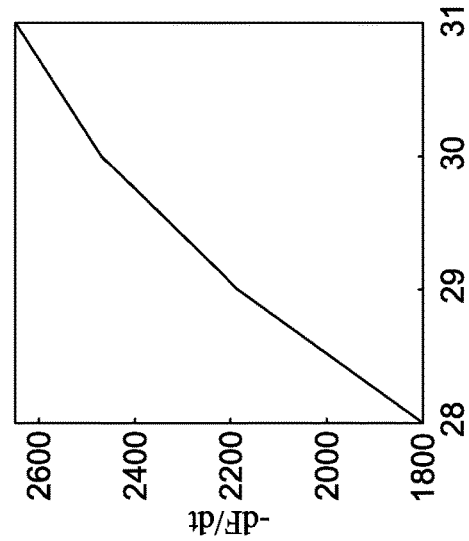
Figure 23A:
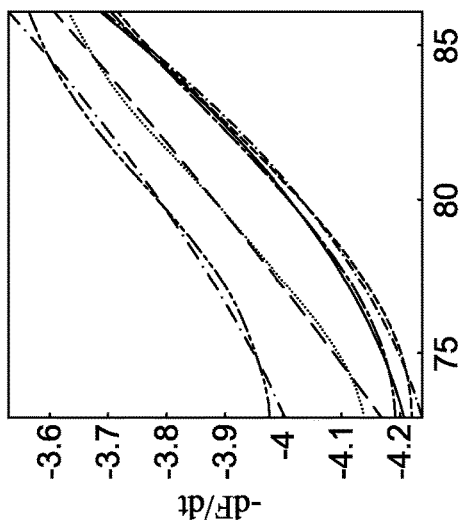
FIGS. 23A-E are similar to FIGS. 22A-E, except for a negative assay for MERS.
Figure 23C:
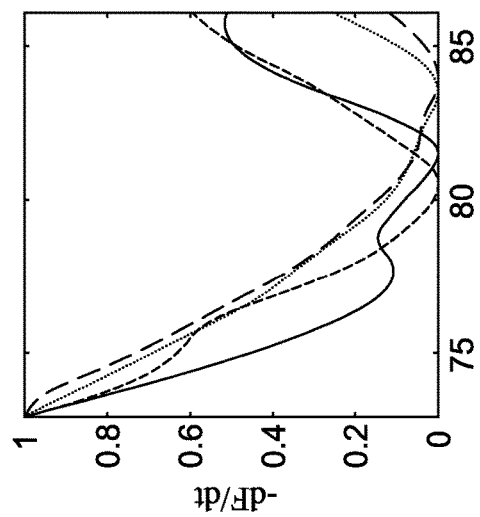
Figure 23B:
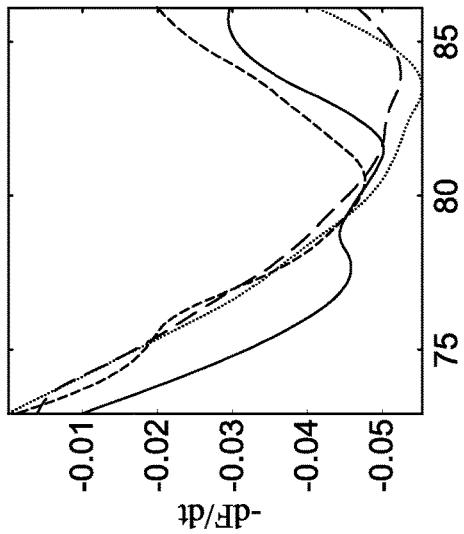
Figure 23D:
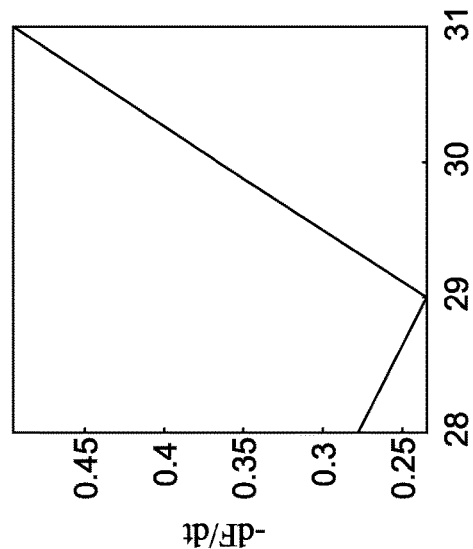
Figure 23E:
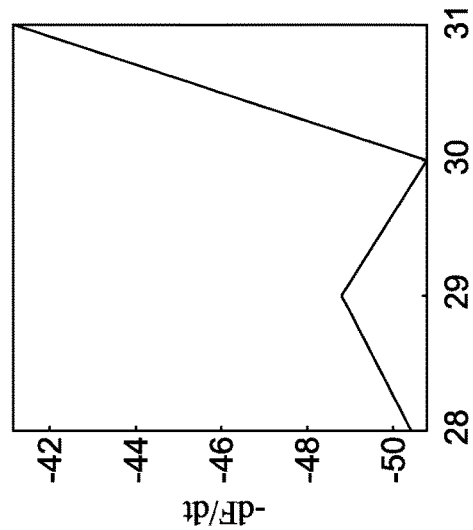

FIG. 22C shows the same four curves of FIG. 22A after they have individually been normalized between zero and one. Normalization allows for the comparison of curve shape, despite variation in amplitude. In one illustrative example, for a set of curves $$C=[C_1, C_2, \ldots, C_N] \quad \text{[Equation 2]}$$

a single mean value may be calculated from the pointwise difference in between a curve and its neighbor, illustratively using:

$$\text{Similarity Metric} = \Sigma_{i=2}^{N} \|C_i - C_{i-1}\| \quad \text{[Equation 3]}$$

where the symbol $\|\cdot\|$ denotes the $l^2$ vector norm defined for a vector $$x=[x_1, x_2, \ldots, x_n] \quad \text{[Equation 4]}$$

as $$\|x\| = \sqrt{\Sigma_{j=1}^{n} |x_j|^2} \quad \text{[Equation 5]}$$

It is expected that a late amplifying sample will exhibit in-cycle melting curves that are very similar in shape. The presented metric should be low when curves are similar, and high when they are not, contributing to a positive or negative melt decision. In FIG. 22C, the similarity metric is quite low: 0.0599. A threshold could be set for this metric. In one illustrative example, a mean L2 metric less than 5 indicates a positive sample. In another illustrative example, a threshold of less than 4 or of 6 may indicate a positive sample. Other thresholds are possible.

FIGS. 23A-E show similar results for a negative assay for MERS. The AUC trend slope is negative, and the similarity metric is high: 5.135.

It is understood that this is just one method of determining the extent of calculating the similarity between curves, and that other methods may be used.

EXAMPLE 12

Figure 24:
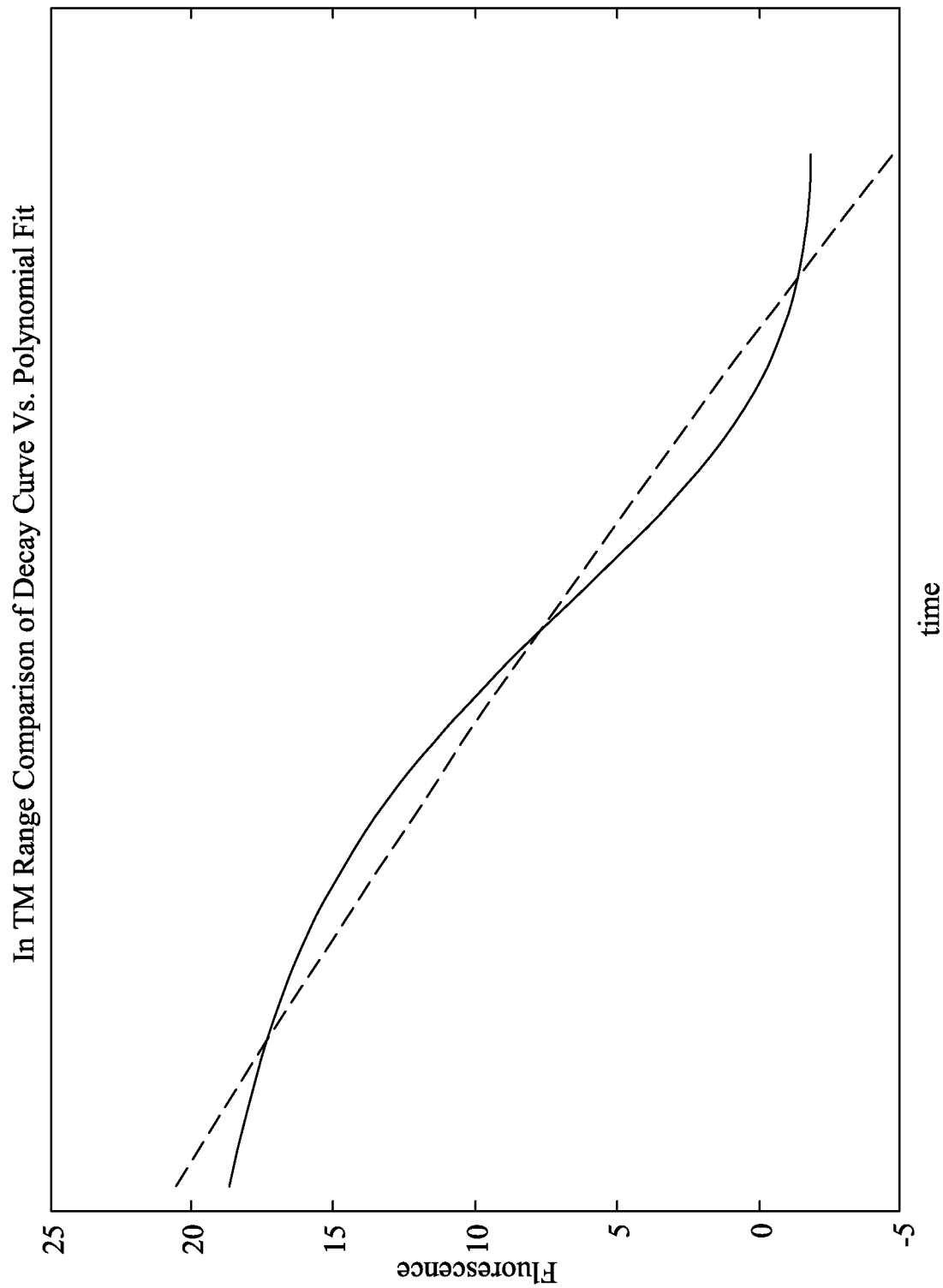
FIG. 24 shows a comparison of fluorescence decay data to a polynomial fit, wherein the solid line is the fluorescence decay curve and the dashed line is a polynomial fit of decay.

In another example illustrated in FIG. 24, similar metrics can be generated from a fit of the fluorescence decay data. A polynomial fit of degree n is defined as the least squares fit of the data x to the equation.

$$p(x) = p_1 x^n + p_2 x^{n-1} + \ldots + p_n x + p_{n+1} \quad \text{[Equation 6]}$$

This fit can be applied to decay curves, and observations can be made about the goodness of fit. It is expected that a high sum residual would indicate that a sample is indeed present and displaying a unique melting curve. Similarly, it is expected that a low residual would indicate background decay and the lack of an amplifying sample. Thresholds for "high" and "low" residuals in this case could be predetermined using experimental data. Fit residuals can be used in this manner, similar to how AUC was used above to infer detection information. Illustratively for this example a residual sum less than 10 could indicate a negative sample, but other cut-off values are possible. The above four examples are meant to illustrate how a group of in cycle melting curves could be used to perform the same function as a traditional high resolution melt. These metrics are intended to be illustrative only, as many other metrics could be devised.

Figure 25:
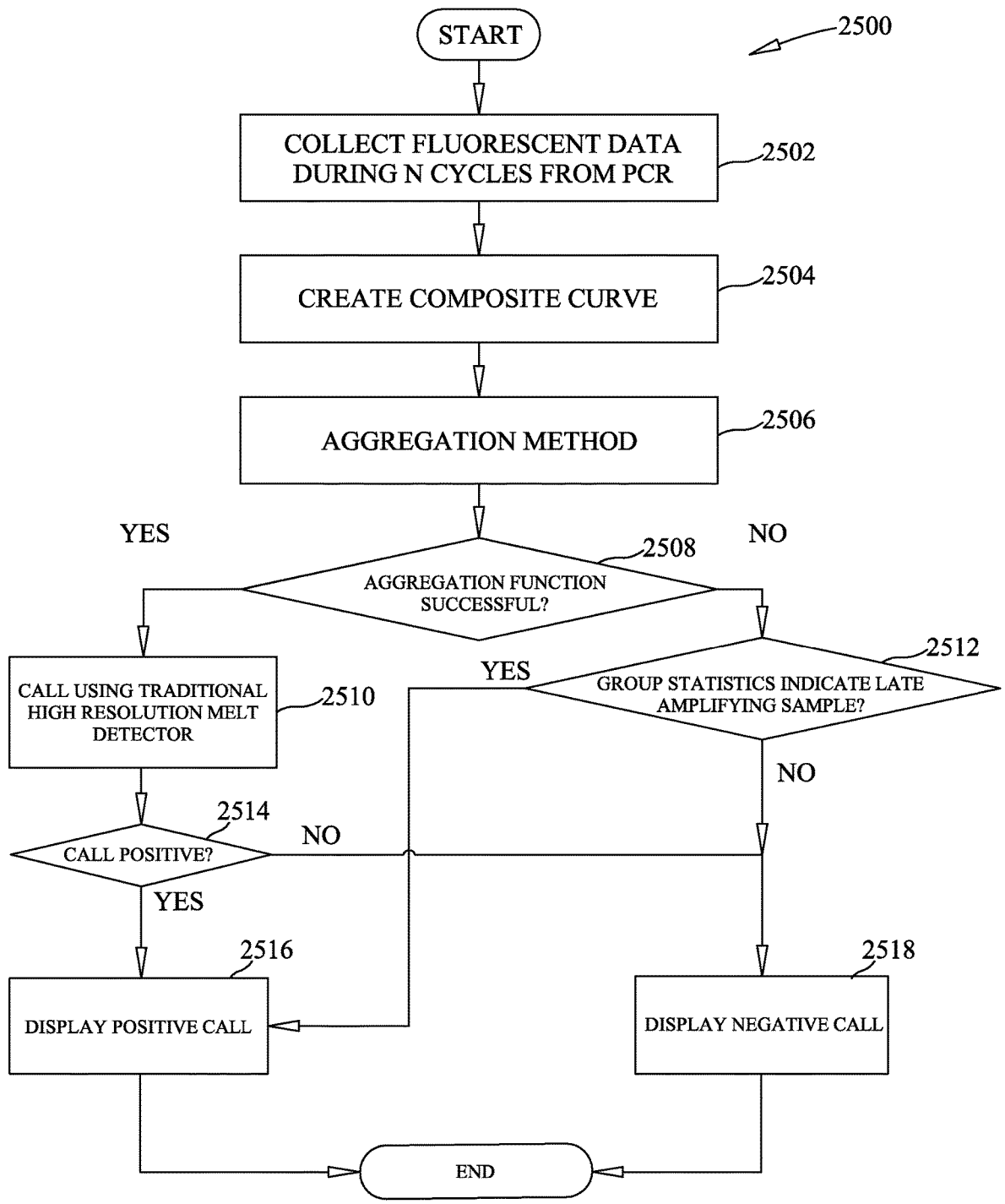
FIG. 25 is a flow chart of an illustrative example of using in-cycle melting curves to make positive and negative calls.
Figure 26:
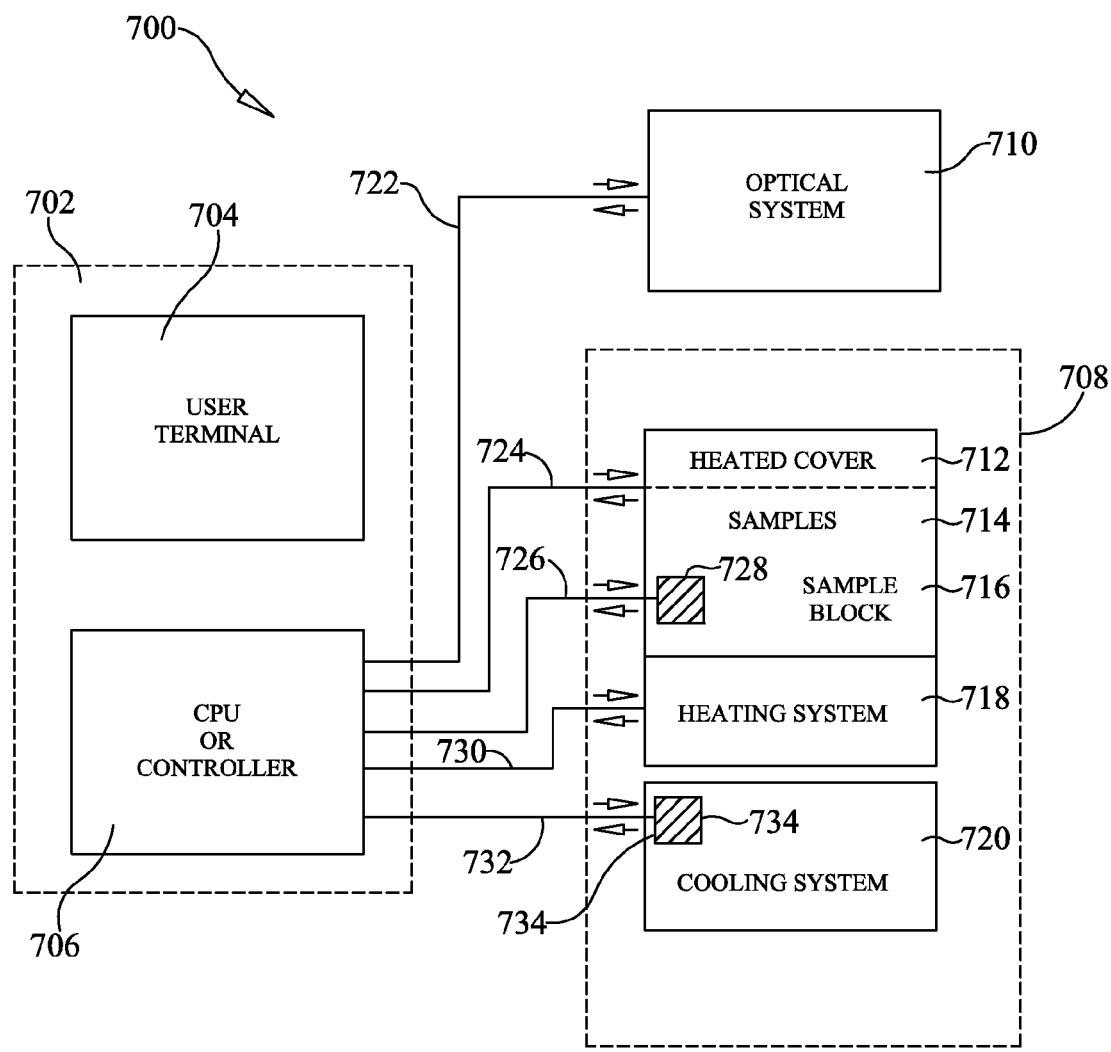
FIG. 26 illustrates a block diagram of an exemplary embodiment of a thermal cycling system in accordance with aspects of the disclosure.

FIG. 25 shows an illustrative process 2500 for using N cycles of in-cycle melting curves to generate a positive or negative call. The process may be implemented by various components of the PCR system as described below with reference to FIG. 26, including a processor or controller, an optical element, and one or more temperature controlling devices. In some embodiments, the process 2500 or a portion thereof may be implemented in a set of instructions and stored on a computer-readable memory and executable on one or more processors or a controller.

A sample is included in a sample well along with primers for amplifying the target nucleic acid sequence and a fluorescent dye such as a dsDNA binding dye. The sample is amplified via thermal cycling which includes at least a two-step PCR protocol. The PCR protocol may include for each of several cycles, an in-cycle temperature adjusting segment or denaturation segment where the sample well is heated from an annealing temperature to a denaturation temperature and cooled from the denaturation temperature to the annealing temperature. The PCR protocol may also include for each of the several cycles, an extension segment where the temperature is held constant. In some embodiments, the processors or controller provide control signals to a thermocycling element including to heat the sample well, to cool the sample well, and to hold the temperature of the sample well constant.

Then at block 2502, fluorescent data (which indicates an amount of fluorescence emitted by the sample) is collected from the sample during the in-cycle temperature adjusting segment for each of N cycles, where N is 2, 3, 4, 5, 6, or more cycles. The fluorescent data may be collected by an optical system such as the optical system 710 as described in more detail below with reference to FIG. 26 and provided to the processors or controller. For example, the optical system may provide light to the sample (e.g., from an LED) and may include optical detectors to detect the amount of light scattered by the sample. In some embodiments, the processors or controller provide control signals to the optical system 710 to detect the amount of light scattered by the sample during the in-cycle temperature adjusting segment for each of the N cycles. The processors or controller may then collect an amount of fluorescence along with a temperature of the sample (temperature, fluorescence pairs) at several points in time during each of the N cycles. It is understood that fluorescence is illustrative only, and other ways of measuring denaturation are within the scope of this disclosure.

At block 2504, a composite melting curve is generated by combining the fluorescent data from each of the N cycles during the respective in-cycle temperature adjusting segments. In some embodiments, for each of the N cycles, the amount of fluorescence may be plotted as a function of temperature to generate an individual melting curve. Each individual melting curve may be normalized for example by scaling between 0 and 1 such that the maximum fluorescence value for an individual melting curve is 1 and the minimum value is 0. The data points from the normalized curves may be combined for each of the N cycles to generate the composite melting curve.

More specifically, to fit the composite melting curve to the data points from all of the N cycles, an aggregation method is utilized (block 2506). If the composite melting curve generated by the aggregation method has small residuals with respect to the data points (residuals less than a predefined threshold), the composite melting curve may be identified as sufficient for determining a melting call. Then a call is made using a traditional high resolution melt detector (block 2510) such as the melt detectors described in U.S. Pat. Nos. 6,387,621; 6,730,501; and 7,373,253 to interrogate curve shape and background noise to determine if PCR product is present in the sample. In other embodiments, a call may be made by analyzing the composite melting curve to, for example, determine a negative first derivative of the composite melting curve. If the melt peak as determined based on the negative first derivative for the composite melting curve is within a predefined melt window, the sample may be called positive. Otherwise, the sample may be called negative. Other characteristics of the composite melting curve or the negative first derivative of the composite melting curve may also be used to make a call.

If the call is positive, the processors or controller may display an indication of a positive call on a user interface (block 2516). On other hand if the call is negative, the processors or controller may display an indication of a negative call on the user interface (block 2518). In some embodiments, the processors or controller may also display indications of the data points, the individual melting curves, the composite melting curve, the negative first derivative of the individual melting curves or composite melting curve, the AUC for the individual melting curves or composite melting curve, etc.

If the composite melting curve generated by the aggregation method has large residuals with respect to the data points (residuals greater than or equal to a threshold), the processors or controller may analyze the composite melting curve or individual melting curves further to determine whether statistics from the composite melting curve or individual melting curves indicate a late amplifying sample (block 2512).

Such statistics may include the curve shape C of each of the individual melting curves. For example, in some embodiments for a set of curves, $C=[C_1, C_2, \ldots, C_N]$, a similarity metric is determined based on the pointwise difference between a curve and its neighbor. The similarity metric may be determined as Similarity Metric=$\Sigma_{i=2}^{N}\|C_i - C_{i-1}\|$. A late amplifying sample may exhibit in-cycle melting curves that are very similar in shape and thus a late amplifying sample may be identified when the similarity metric is less than a threshold value. A late amplifying sample may be also be identified using other statistics such as values of AUC for each of the individual melting curves. More specifically, the average slope of the AUC for the individual melting curves may be used to identify a late amplifying sample, such as when the average slope depicts a linear trend with a positive slope indicating that the AUC increases each cycle. Any other suitable statistics from the composite melting curve and/or individual melting curves may also be utilized to identify a late amplifying sample including similar peak locations, for assays that have not yet plateaued, a growing AUC, similar curve shape based on a quadratic fit, a polynomial least squares fit or other type of fit, or other features to distinguish amplified and amplifying assays from negative assays.

In any event, when a late amplifying sample is identified, the processors or controller may make a positive call and display an indication of the positive call on the user interface (block 2516). On the other hand when a late amplifying sample is not identified for example when the similarity metric is not less than a threshold value, the processors or controller may make a negative call and display an indication of the negative call on the user interface (block 2518). In some embodiments, if a value is too close to the threshold, the processor may return an "indeterminate" call. In such embodiments, rather than setting a single value for the threshold, a range could be set wherein values within that range would return an indeterminate call.

While a single threshold value on individual metrics may suffice for obvious calls, samples very close to the limit of detection may pose a problem. It is understood that a more intricate calling algorithm could make use of many of the metrics listed above or others, when used in concert. For example, if a sample has a low sum AUC, the slope and Tm locations could be considered. Machine learning algorithms such as a decision tree could be employed to optimize these complicated decision pathways to generate a more robust detection system.

EXAMPLE 13

Certain embodiments of the present invention may also involve or include a PCR system configured to make positive or negative calls from amplification curves or melting curves or a combination thereof. Illustrative examples are described in U.S. Pat. No. 8,895,295, already incorporated by reference, for use with pouch 510 or similar embodiments. However, it is understood that the embodiments described in U.S. Pat. No. 8,895,295 are illustrative only and other systems may be used according to this disclosure. For example, referring to FIG. 26, a block diagram of an illustrative system 700 that includes control element 702, a thermocycling element 708, and an optical element 710 according to exemplary aspects of the disclosure is shown.

In at least one embodiment, the system may include at least one PCR reaction mixture housed in sample vessel 714. In certain embodiments, the sample vessel 714 may include a PCR reaction mixture configured to permit and/or effect amplification of a template nucleic acid. Certain illustrative embodiments may also include at least one sample block or chamber 716 configured to receive the at least one sample vessel 714. The sample vessel 714 may include any plurality of sample vessels in individual, strip, plate, or other format, and, illustratively, may be provided as or received by a sample block or chamber 716.

One or more embodiments may also include at least one sample temperature controlling device 718 and/or 720 configured to manipulate and/or regulate the temperature of the sample(s). Such a sample temperature controlling device may be configured to raise, lower, and/or maintain the temperature of the sample(s). In one example, sample controlling device 718 is a heating system and sample controlling device 720 is a cooling system. Illustrative sample temperature controlling devices include (but are not limited to) heating and/or cooling blocks, elements, exchangers, coils, radiators, refrigerators, filaments, Peltier devices, forced air blowers, handlers, vents, distributors, compressors, condensers, water baths, ice baths, flames and/or other combustion or combustible forms of heat, hot packs, cold packs, dry ice, dry ice baths, liquid nitrogen, microwave- and/or other wave-emitting devices, means for cooling, means for heating, means for otherwise manipulating the temperature of a sample, and/or any other suitable device configured to raise, lower, and/or maintain the temperature of the sample(s).

The illustrative PCR system 700 also includes an optical system 710 configured to detect an amount of fluorescence emitted by the sample 714 (or a portion or reagent thereof). Such an optical system 710 may include one or more fluorescent channels, as are known in the art, and may simultaneously or individually detect fluorescence from a plurality of samples.

At least one embodiment of the PCR system may further include a CPU 706 programmed or configured to operate, control, execute, or otherwise advance the heating system 718 and cooling system 720 to thermal cycle the PCR reaction mixture, illustratively while optical system 710 collects fluorescent signal. CPU 706 may then generate an amplification curve, a melting curve, or any combination, which may or may not be printed, displayed on a screen of the user terminal 704, or otherwise outputted. Optionally, a positive, negative, or other call may be outputted based on the amplification and/or melting curve for example on the screen of the user terminal 704. Optionally only the calls are outputted, illustratively one call for each target tested.

The CPU 706 may include a program memory, a microcontroller or a microprocessor (MP), a random-access memory (RAM), and an input/output (I/O) circuit, all of which are interconnected via an address/data bus. The program memory may include an operating system such as Microsoft Windows®, OS X®, Linux®, Unix®, etc. In some embodiments, the CPU 706 may also include, or otherwise be communicatively connected to, a database or other data storage mechanism (e.g., one or more hard disk drives, optical storage drives, solid state storage devices, etc.). The database may include data such as melting curves, annealing temperatures, denaturation temperatures, and other data necessary to generate and analyze melting curves. The CPU 706 may include multiple microprocessors, multiple RAMS, and multiple program memories as well as a number of different types of I/O circuits. The CPU 706 may implement the RAM(s) and the program memories as semiconductor memories, magnetically readable memories, and/or optically readable memories, for example.

The microprocessors may be adapted and configured to execute any one or more of a plurality of software applications and/or any one or more of a plurality of software routines residing in the program memory, in addition to other software applications. One of the plurality of routines may include a thermocycling routine which may include providing control signals to the heating system 718 and the cooling system 720 to heat and cool the sample 714 respectively, in accordance with the two-step PCR protocol. Another of the plurality of routines may include a fluorescence routine which may include providing control signals to the optical system 710 to emit a fluorescence signal and detect the amount of fluorescence scattered by the sample 714. Yet another of the plurality of routines may include a sample calling routine which may include obtaining fluorescence data (temperature, fluorescence pairs) from the optical system 710 during the in-cycle temperature adjusting segment for each of N cycles, generating a composite melting curve by combining the fluorescent data from each of the N cycles during the respective in-cycle temperature adjusting segments, analyzing the composite melting curve to make a positive or negative call, and displaying the composite melting curve, individual melting curve, and/or an indication of the call on the user terminal 704.

In some embodiments, the CPU 706 may communicate with the user terminal 704, the heating system 718, the cooling system 720, the optical system 710, and the sample block 716 over a communication network 722-732 via wired or wireless signals and, in some instances, may communicate over the communication network via an intervening wireless or wired device, which may be a wireless router, a wireless repeater, a base transceiver station of a mobile telephony provider, etc. The communication network may be a wireless communication network such as a fourth- or third-generation cellular network (4G or 3G, respectively), a Wi-Fi network (802.11 standards), a WiMAX network, a wide area network (WAN), a local area network (LAN), the Internet, etc. Furthermore, the communication network may be a proprietary network, a secure public Internet, a virtual private network and/or some other type of network, such as dedicated access lines, plain ordinary telephone lines, satellite links, combinations of these, etc. Where the communication network comprises the Internet, data communication may take place over the communication network via an Internet communication protocol. Still further, the communication network may be a wired network where data communication may take place via Ethernet or a Universal Serial Bus (USB) connection.

In some embodiments, the CPU 706 may be included within the user terminal 704. In other embodiments, the CPU 706 may communicate with the user terminal 704 via a wired or wireless connection (e.g., as a remote server) to display individual melting curves, composite melting curves, calls, etc. on the user terminal 704. The user terminal 704 may include a user interface, a communication unit, and a user-input device such as a "soft" keyboard that is displayed on the user interface of the user terminal 704, an external hardware keyboard communicating via a wired or a wireless connection (e.g., a Bluetooth keyboard), an external mouse, or any other suitable user-input device in addition to the CPU 706 or another CPU similar to the CPU 706.

Additional examples of illustrative features, components, elements, and or members of illustrative PCR systems and/or thermal cyclers (thermocyclers) are known in the art and/or described above or in U.S. Patent Application No. 2014-0273181, the entirety of which is herein incorporated by reference.

Aspects

Embodiments of the techniques described in the present disclosure may include any number of the following aspects, either alone or combination:

1. A method for calling a sample for a target nucleic acid sequence comprising (a) providing a sample well with the sample, primers configured for amplifying the target nucleic acid sequence, a fluorescent dye, and components for amplification, (b) amplifying the sample by thermal cycling the sample well between at least an annealing temperature and a denaturation temperature through a plurality of cycles, wherein each cycle includes an in-cycle denaturation step, (c) collecting fluorescent data during the in-cycle denaturation step of n cycles wherein n is at least two, (d) generating a composite melting curve using the fluorescent data collected during the denaturation step of each of the n cycles, and (e) calling the sample using the composite melting curve, wherein the call is selected from at least a positive or a negative call.

2. The method according to aspect 1, wherein step (e) includes generating a melt peak, if the melt peak is within a predefined melt window, the sample is called positive and if the melt peak is not within the predefined melt window, the sample is called negative.

3. The method according to any one of the preceding aspects, wherein step (e) includes fitting the composite melting curve using an aggregation method, and if residuals are smaller than a predetermined threshold value, the sample is called positive.

4. The method according to any one of the preceding aspects, wherein if the residuals are larger than the threshold value the in-cycle melting curves are analyzed further.

5. The method according to any one of the preceding aspects, wherein the threshold is a range, and the calling step includes calling the sample indeterminate when the residuals are within the range.

6. The method according to any one of the preceding aspects, wherein step (e) includes generating individual melting curves for the in-cycle denaturation step for each of the n cycles, and calculating an area under a curve for each of the individual melting curves.

7. The method according to any one of the preceding aspects, further comprising calling the sample positive if the area under the curve increases each cycle.

8. The method according to any one of the preceding aspects, further comprising normalizing the individual melting curves and calling the sample positive if the curves are similar 9. The method according to any one of the preceding aspects, further using a similarity metric to determine if the curves are similar.

10. The method according to any one of the preceding aspects, wherein the similarity metric uses the following formula:

$$\text{Similarity Metric} = \Sigma_{i=2}^{N} \|C_i - C_{i-1}\|\mu.$$

11. A system for calling a sample positive or negative for a target nucleic acid sequence, the system comprising: a sample well configured to house the sample, the sample well comprising the target nucleic acid and components for amplification; one or more temperature controlling devices configured to amplify the sample by thermal cycling the sample well including heating the sample well to a first temperature and cooling the sample well to a second temperature through a plurality of cycles, wherein each cycle includes an in-cycle temperature adjusting segment, an optical system configured to detect an amount of fluorescence emitted by the sample; a controller configured to: receive data indicative of the amount of fluorescence emitted by the sample from an optical system during the in-cycle temperature adjusting segment for two or more of the plurality of cycles; generate a composite melting curve by combining the data from each of the two or more cycles; analyze the composite melting curve to call the sample negative or positive; and display an indication of the negative or positive call for the sample.

12. The system according to aspect 11, wherein the first temperature is a denaturation temperature and the second temperature is an annealing temperature.

13. The system according to either one of aspect 11 or aspect 12, wherein the in-cycle temperature adjusting segment is a denaturation segment that includes increasing a temperature of the sample from the annealing temperature to the denaturation temperature and decrease the temperature of the sample from the denaturation temperature to the annealing temperature, and wherein each cycle further includes an extension segment that includes holding the temperature constant.

14. The system according to any one of aspects 11-13, wherein to analyze the composite melting curve to call the sample negative or positive, the controller is configured to: generate a melt peak based on the composite melting curve; call the sample positive when the melt peak is within a predefined melt window; and call the sample negative when the melt peak is not within the predefined melt window.

15. The system according to any one of aspects 11-14, wherein to analyze the composite melting curve to call the sample negative or positive, the controller is configured to: fit the composite melting curve with an aggregation method; and call the sample positive when residuals are less than a predefined threshold.

16. The system according to any one of aspects 11-15, wherein the controller is further configured to: analyze the composite melting curve further when the residuals are greater than or equal to the threshold.

17. The system according to any one of aspects 11-16, wherein the threshold is a range, and the controller is also configured to display an indeterminate call when the residuals are within the range.

18. The system according to any one of aspects 11-17, wherein to analyze the composite melting curve to call the sample negative or positive, the controller is configured to: generate individual melting curves for the in-cycle temperature adjusting segment for each of the two or more cycles; and calculate an area under a curve for each of the individual melting curves.

19. The system according to any one of aspects 11-18, wherein the controller is further configured to: call the sample positive when the area under the curve increases each cycle according to the individual melting curves.

20. The system according to any one of aspects 11-19, wherein the controller is further configured to: normalize the individual melting curves; determine a similarity metric for the normalized melting curves; and call the sample positive when the similarity metric is less than a threshold value.

21. The system according to any one of aspects 11-20, wherein the similarity metric is determined as: Similarity Metric=$\Sigma_{i=2}^{N}\|C_i-C_{i-1}\|\mu$, wherein $C_i$ indicates a shape of a curve for individual melting curve I, wherein N is a number of the two or more cycles, and wherein the symbol $\|\cdot\|$ denotes the $l^2$ vector norm defined for a vector $x=[x_1, x_2, \ldots, x_n]$ as $\|x\| = \sqrt{\Sigma_{j=1}^{n}\|x_j\|^2}$.

22. The system according to any one of aspects 11-21, wherein at least one of the temperature controlling devices is configured to heat the sample well at a temperature transition greater than 3° C./sec while the controller is receiving the data indicative of the amount of fluorescence emitted by the sample from an optical system during the in-cycle temperature adjusting segment for two or more of the plurality of cycles used to generate the composite melting curve.

23. The system according to any one of aspects 11-22, wherein the target nucleic acid sequence is from a pathogen.

24. A computing device for calling a sample for a target nucleic acid sequence comprising: one or more processors; and a non-transitory computer-readable memory coupled to the one or more processors and storing thereon instructions that, when executed by the one or more processors, cause the computing device to: provide control signals to a thermocycling element that include heating the sample to a first temperature and cooling the sample to a second temperature through a plurality of cycles, wherein each cycle includes an in-cycle temperature adjusting segment; receive data indicative of the amount of fluorescence emitted by the sample from an optical system during the in-cycle temperature adjusting segment for two or more of the plurality of cycles; generate a composite melting curve by combining the data from each of the two or more cycles; analyze the composite melting curve to call the sample negative or positive; and display an indication of the call for the sample, wherein the call is selected from at least the positive or negative call.

25. The computing device according to aspect 24, wherein the first temperature is a denaturation temperature and the second temperature is an annealing temperature.

26. The computing device according to either one of aspect 24 or aspect 25, wherein the in-cycle temperature adjusting segment is a denaturation segment that includes increasing a temperature of the sample from the annealing temperature to the denaturation temperature and decreasing the temperature of the sample from the denaturation temperature to the annealing temperature, and wherein each cycle further includes an extension segment in which the instructions cause the computing device to provide control signals to the thermocycling element to hold the temperature constant.

27. The computing device according to any one of aspects 24-26, wherein to analyze the composite melting curve to call the sample negative or positive, the instructions cause the computing device to: generate a melt peak based on the composite melting curve; call the sample positive when the melt peak is within a predefined melt window; and call the sample negative when the melt peak is not within the predefined melt window.

28. The computing device according to any one of aspects 24-27, wherein to analyze the composite melting curve to call the sample negative or positive, the instructions cause the computing device to: fit the composite melting curve using an aggregation method; and call the sample positive when residuals are less than a predefined threshold.

29. The computing device according to any one of aspects 24-28, wherein the instructions further cause the computing device to: analyze the composite melting curve further when the residuals are greater than or equal to the threshold.

30. The computing device according to any one of aspects 24-29, wherein the threshold is a range, and the instructions cause the computing device to call the sample indeterminate when the residuals are within the range.

31. The computing device according to any one of aspects 24-30, wherein to analyze the composite melting curve to call the sample negative or positive, the instructions cause the computing device to: generate individual melting curves for the in-cycle temperature adjusting segment for each of the two or more cycles; and calculate an area under a curve for each of the individual melting curves.

32. The computing device according to any one of aspects 24-31, wherein the instructions further cause the computing device to: call the sample positive when the area under the curve increases each cycle according to the individual melting curves.

33. The computing device according to any one of aspects 24-32, wherein the instructions further cause the computing device to: normalize the individual melting curves; determine a similarity metric for the normalized melting curves; and call the sample positive when the similarity metric is less than a threshold value.

34. The computing device according to any one of aspects 24-33, wherein the similarity metric is determined as: Similarity Metric=$\Sigma_{i=2}^{N}\|C_i-C_{i-1}\|$, wherein $C_i$ indicates a shape of a curve for individual melting curve I, wherein N is a number of the two or more cycles, and wherein the symbol $\|\cdot\|$ denotes the $l^2$ vector norm defined for a vector x=[$x_1$, $x_2$, ..., $x_n$] as $\|x\|=\sqrt{\Sigma_{j=1}^{n}\|x_j\|^2}$.

35. A method for calling a sample positive or negative for a target nucleic acid sequence comprising: providing a sample well that houses the sample, amplifying the sample by thermal cycling the sample well including heating the sample well to a first temperature and cooling the sample well to a second temperature through a plurality of cycles, wherein each cycle includes an in-cycle temperature adjusting segment, collecting data indicative of the amount of fluorescence emitted by the sample during the in-cycle temperature adjusting segment for two or more of the plurality of cycles, generating, by one or more processors, a composite melting curve by combining the data from each of the two or more cycles, analyzing, by the one or more processors, the composite melting curve to call the sample negative or positive, and displaying, by the one or more processors, an indication of the negative or positive call for the sample.

Although the invention has been described in detail with reference to preferred embodiments, variations and modifications exist within the scope and spirit of the invention as described and defined in the following claims.

The invention claimed is:

1. A system for calling a sample positive or negative for a target nucleic acid sequence, the system comprising:
   a sample well configured to house the sample, the sample well comprising the target nucleic acid and components for amplification;
   one or more temperature controlling devices configured to amplify the sample by thermal cycling the sample well including heating the sample well to a first temperature and cooling the sample well to a second temperature through a plurality of cycles, wherein each cycle includes an in-cycle temperature adjusting segment,
   an optical system configured to detect an amount of fluorescence emitted by the sample;
   a controller configured to:
      receive data indicative of the amount of fluorescence emitted by the sample from an optical system during the in-cycle temperature adjusting segment for two or more of the plurality of cycles;
      generate a composite melting curve by combining the data from each of the two or more cycles including fitting the composite melting curve using an aggregation method;
      analyze the composite melting curve to call the sample negative or positive; and
      display an indication of the negative or positive call for the sample.

2. The system of claim 1, wherein the first temperature is a denaturation temperature and the second temperature is an annealing temperature.

3. The system of claim 2, wherein the in-cycle temperature adjusting segment is a denaturation segment that includes increasing a temperature of the sample from the annealing temperature to the denaturation temperature and decrease the temperature of the sample from the denaturation temperature to the annealing temperature, and wherein each cycle further includes an extension segment that includes holding the temperature constant.

4. The system of claim 1, wherein to analyze the composite melting curve to call the sample negative or positive, the controller is configured to:
   generate a melt peak based on the composite melting curve;
   call the sample positive when the melt peak is within a predefined melt window; and
   call the sample negative when the melt peak is not within the predefined melt window.

5. The system of claim 1, wherein to analyze the composite melting curve to call the sample negative or positive, the controller is configured to:
   call the sample positive when residuals are less than a predefined threshold.

6. The system of claim 5, wherein the controller is further configured to:
    analyze the composite melting curve further when the residuals are greater than or equal to the threshold to determine whether statistics from the composite melting curve indicate a late amplifying sample.

7. The system of claim 6, wherein the threshold is a range, and the controller is also configured to display an indeterminate call when the residuals are within the range.

8. A computing device for calling a sample for a target nucleic acid sequence comprising:
    one or more processors; and
    a non-transitory computer-readable memory coupled to the one or more processors and storing thereon instructions that, when executed by the one or more processors, cause the computing device to:
        provide control signals to a thermocycling element that include heating the sample to a first temperature and cooling the sample to a second temperature through a plurality of cycles, wherein each cycle includes an in-cycle temperature adjusting segment;
        receive data indicative of the amount of fluorescence emitted by the sample from an optical system during the in-cycle temperature adjusting segment for two or more of the plurality of cycles;
        generate a composite melting curve by combining the data from each of the two or more cycles including fitting the composite melting curve using an aggregation method;
        analyze the composite melting curve to call the sample negative or positive; and
        display an indication of the call for the sample, wherein the call is selected from at least the positive or negative call.

9. The computing device of claim 8, wherein the first temperature is a denaturation temperature and the second temperature is an annealing temperature.

10. The computing device of claim 9, wherein the in-cycle temperature adjusting segment is a denaturation segment that includes increasing a temperature of the sample from the annealing temperature to the denaturation temperature and decreasing the temperature of the sample from the denaturation temperature to the annealing temperature, and wherein each cycle further includes an extension segment in which the instructions cause the computing device to provide control signals to the thermocycling element to hold the temperature constant.

* * * * *